US010822664B2

(12) United States Patent
Rey

(10) Patent No.: US 10,822,664 B2
(45) Date of Patent: Nov. 3, 2020

(54) SEQUENCE-SPECIFIC DETECTION AND PHENOTYPE DETERMINATION

(71) Applicant: GeneWeave Biosciences, Inc., Los Gatos, CA (US)

(72) Inventor: Diego Ariel Rey, San Francisco, CA (US)

(73) Assignee: Roche Molecular Systems Inc., Pleasanton, CA (US)

( * ) Notice: Subject to any disclaimer, the term of this patent is extended or adjusted under 35 U.S.C. 154(b) by 0 days.

(21) Appl. No.: 16/245,093

(22) Filed: Jan. 10, 2019

(65) Prior Publication Data

US 2019/0127810 A1 May 2, 2019

Related U.S. Application Data

(62) Division of application No. 15/136,646, filed on Apr. 22, 2016, now Pat. No. 10,227,661.

(60) Provisional application No. 62/155,011, filed on Apr. 30, 2015.

(51) Int. Cl.
*C12Q 1/689* (2018.01)
*C12Q 1/6897* (2018.01)

(52) U.S. Cl.
CPC ........... *C12Q 1/6897* (2013.01); *C12Q 1/689* (2013.01)

(58) Field of Classification Search
None
See application file for complete search history.

(56) References Cited

U.S. PATENT DOCUMENTS 6,274,316 B1 * 8/2001 Modrusan ............ C12Q 1/6823 435/5
2011/0269130 A1 * 11/2011 Shi ........................... C12Q 1/18 435/6.11

FOREIGN PATENT DOCUMENTS

WO WO-0112803 A2 * 2/2001 ......... C12N 15/1137
WO WO-2014160418 A2 * 10/2014 ............... C12Q 1/18

OTHER PUBLICATIONS

Kurupati et al. 2007 (Inhibition of Gene Expression and Growth by Antisense Peptide Nucleic Acids in a Multiresistant b-lactamase-producing Klebsiella pneumonia strain; Antimicrobial Agents and Chemotherapy 51(3): 805-811). (Year: 2007).*
Walsh 2000 (Molecular mechanisms that confer antibacterial drug resistance; Nature 406: 775-781) (Year: 2000).*

* cited by examiner

*Primary Examiner* — Mary Maille Lyons
(74) *Attorney, Agent, or Firm* — David J. Chang

(57) ABSTRACT

Disclosed herein are materials and methods for achieving sequence-specific organism detection and/or phenotype(s) using sequence-specific oligonucleotides. Also disclosed are related kits, cultures, and cells for detecting and/or phenotyping microorganisms in a sequence-specific manner.

4 Claims, 9 Drawing Sheets

Specification includes a Sequence Listing.

| | 1 | 2 | 3 | 4 | 5 |
|---|---|---|---|---|---|
| E. coli strain | Reporter | Reporter + meropenem | Reporter + meropenem + kpc peptide-PNA | Reporter + meropenem + ndm-1 peptide-PNA | Reporter + kpc or ndm-1 peptide-PNA |
| 1289011 | + | + | + | + | + |
| 1289012 | + | + | - | + | + |
| 1289014 | + | + | + | - | + |
| 1289018 | + | - | - | - | + |

FIG. 5

| | 1 | 2 | 3 | 4 |
|---|---|---|---|---|
| *E. coli* strain | *bla*$_{NDM-1}$ NRTP + meropenem | *bla*$_{SHV-18}$ NRTP + meropenem | *bla*$_{NDM-1}$ NRTP + ceftazidime | *bla*$_{SHV-18}$ NRTP + ceftazidime |
| 1289018 | - | - | - | - |
| 1289023 | - | + | - | + |
| 1289027 | - | - | + | - |
| 1289011 | + | + | + | + |

FIG. 6

| | | | 1 | 2 | 3 | 4 |
|---|---|---|---|---|---|---|
| Strain | *Enterococcus spp.* | vancomycin-resistance gene | Reporter | Reporter + vancomycin | Reporter + vancomycin + *vanC* Peptide-PNA | Reporter + *vanC* Peptide-PNA |
| 1259012 | *E. faecalis* | none | + | - | - | + |
| 1259016 | *E. faecalis* | *vanA* | + | + | + | + |
| 1269011 | *E. faecium* | none | + | - | - | + |
| 1269014 | *E. faecium* | *vanB* | + | + | + | + |
| 1279015 | *E. gallinarum* | *vanC* | + | + | - | + |

FIG. 7

| Strain | Species | ITS2-based AON | ITS2 Genbank Sequence |
|---|---|---|---|
| S120012 | *Candida albicans* | 1 | AB049120 |
| S160014 | *Candida tropicalis* | 2 | AM117838 |
| S150013 | *Candida parapsilosis* | 3 | AJ635316 |

FIG. 8

| | | | 1 | 2 | 3 | 4 | 5 |
|---|---|---|---|---|---|---|---|
| Strain | Species | ITS2-based AON | Reporter | Reporter + AON 2, 3 | Reporter + AON 1, 3 | Reporter + AON 1, 2 | Reporter + AON 1, 2, 3 |
| S120012 | *Candida albicans* | 1 | + | + | - | - | - |
| S160014 | *Candida tropicalis* | 2 | + | - | + | - | - |
| S150013 | *Candida parapsilosis* | 3 | + | - | - | + | - |

FIG. 9

SEQUENCE LISTING

```
<160> NUMBER OF SEQ ID NOS: 14

<210> SEQ ID NO 1
<211> LENGTH: 10
<212> TYPE: DNA
<213> ORGANISM: Artificial Sequence
<220> FEATURE:
<223> OTHER INFORMATION: E. Coli murA-targetting peptide nucleic acid
      sequence

<400> SEQUENCE: 1

ccatttagtt                                                            10


<210> SEQ ID NO 2
<211> LENGTH: 10
<212> TYPE: DNA
<213> ORGANISM: Artificial Sequence
<220> FEATURE:
<223> OTHER INFORMATION: blaKPC-3-targetting peptide nucleic acid
      sequence

<400> SEQUENCE: 2

tcaacgatat                                                            10


<210> SEQ ID NO 3
<211> LENGTH: 11
<212> TYPE: DNA
<213> ORGANISM: Artificial Sequence
<220> FEATURE:
<223> OTHER INFORMATION: blaNDM-1-targetting peptide nucleic acid
      sequence

<400> SEQUENCE: 3

tcaagttttc c                                                          11


<210> SEQ ID NO 4
<211> LENGTH: 4549
<212> TYPE: DNA
<213> ORGANISM: Artificial Sequence
<220> FEATURE:
<223> OTHER INFORMATION: CRISPR/Cas9 system targeting blaNDM-1

<400> SEQUENCE: 4

tccctatcag tgatagagat tgacatccct atcagtgata gagatactga gcacatcagc      60

aggacgcact gaccgaattc attaaagagg agaaaggtgc ggccgcatgc atcaccatca     120

ccatcacatg gataagaaat actcaatagg cttagatatc ggcacaaata gcgtcggatg     180

ggcggtgatc actgatgaat ataaggttcc gtctgttcaa ggttctggga aatacagacc     240
```

-continued

```
gccacagtat caaaaaaaat cttatagggg ctcttttatt tgacagtgga gagacagcgg    300

aagcgactcg tctcaaacgg acagctcgta gaaggtatac acgtcggaag aatcgtattt    360

gttatctaca ggagattttt tcaaatgaga tggcgaaagt agatgatagt ttctttcatc    420

gacttgaaga gtctttttg gtggaagaag acaagaagca tgaacgtcat cctatttttg    480

gaaatatagt agatgaagtt gcttatcatg agaaatatcc aactatctat catctgcgaa    540

aaaaattggt agattctact gataaagcgg atttgcgctt aatctatttg gccttagcgc    600

atatgattaa gtttcgtggt catttttga ttgagggaga tttaaatcct gataatagtg    660

atgtggacaa actatttatc cagttggtac aaacctacaa tcaattattt gaagaaaacc    720

ctattaacgc aagtggagta gatgctaaag cgattctttc tgcacgattg agtaaatcaa    780

gacgattaga aaatctcatt gctcagctcc ccggtgagaa gaaaaatggc ttatttggga    840

atctcattgc tttgtcattg ggtttgaccc ctaattttaa atcaaatttt gatttggcag    900

aagatgctaa attacagctt tcaaaagata cttacgatga tgatttagat aatttattgg    960

cgcaaattgg agatcaatat gctgatttgt ttttggcagc taagaattta tcagatgcta   1020

ttttactttc agatatccta agagtaaata ctgaaataac taaggctccc ctatcagctt   1080

caatgattaa acgctacgat gaacatcatc aagacttgac tcttttaaaa gctttagttc   1140

gacaacaact tccagaaaag tataaagaaa tcttttttga tcaatcaaaa aacggatatg   1200

caggttatat tgatggggga gctagccaag aagaatttta taaatttatc aaaccaattt   1260

tagaaaaaat ggatggtact gaggaattat tggtgaaact aaatcgtgaa gatttgctgc   1320

gcaagcaacg gacctttgac aacggctcta ttccccatca aattcacttg ggtgagctgc   1380

atgctatttt gagaagacaa gaagactttt atccattttt aaaagacaat cgtgagaaga   1440

ttgaaaaaat cttgactttt cgaattcctt attatgttgg tccattggcg cgtggcaata   1500

gtcgttttgc atggatgact cggaagtctg aagaaacaat taccccatgg aatttgaag    1560

aagttgtcga taaaggtgct tcagctcaat catttattga acgcatgaca aactttgata   1620

aaaatcttcc aaatgaaaaa gtactaccaa aacatagttt gctttatgag tattttacgg   1680

tttataacga attgacaaag gtcaaatatg ttactgaagg aatgcgaaaa ccagcatttc   1740

tttcaggtga acagaagaaa gccattgttg atttactctt caaaacaaat cgaaaagtaa   1800

ccgttaagca attaaaagaa gattatttca aaaaaataga atgttttgat agtgttgaaa   1860

tttcaggagt tgaagataga tttaatgctt cattaggtac ctaccatgat ttgctaaaaa   1920

ttattaaaga taaagatttt ttggataatg aagaaaatga agatatctta gaggatattg   1980

ttttaacatt gaccttattt gaagataggg agatgattga ggaaagactt aaaacatatg   2040

ctcacctctt tgatgataag gtgatgaaac agcttaaacg tcgccgttat actggttggg   2100

gacgtttgtc tcgaaaattg attaatggta ttagggataa gcaatctggc aaaacaatat   2160

tagatttttt gaaatcagat ggttttgcca atcgcaattt tatgcagctg atccatgatg   2220

atagtttgac atttaaagaa gacattcaaa aagcacaagt gtctggacaa ggcgatagtt   2280

tacatgaaca tattgcaaat ttagctggta gccctgctat taaaaaaggt attttacaga   2340

ctgtaaaagt tgttgatgaa ttggtcaaag taatggggcg gcataagcca gaaaatatcg   2400

ttattgaaat ggcacgtgaa aatcagacaa ctcaaaaggg ccagaaaaat tcgcgagagc   2460

gtatgaaacg aatcgaagaa ggtatcaaag aattaggaag tcagattctt aaagagcatc   2520

ctgttgaaaa tactcaattg caaaatgaaa agctctatct ctattatctc caaaatggaa   2580

gagacatgta tgtggaccaa gaattagata ttaatcgttt aagtgattat gatgtcgatc   2640
```

acattgttcc acaaagtttc cttaaagacg attcaataga caataaggtc ttaacgcgtt 2700
ctgataaaaa tcgtggtaaa tcggataacg ttccaagtga agaagtagtc aaaaagatga 2760
aaaactattg gagacaactt ctaaacgcca agttaatcac tcaacgtaag tttgataatt 2820
taacgaaagc tgaacgtgga ggtttgagtg aacttgataa agctggtttt atcaaacgcc 2880
aattggttga aactcgccaa atcactaagc atgtggcaca aattttggat agtcgcatga 2940
atactaaata cgatgaaaat gataaactta ttcgagaggt taaagtgatt accttaaaat 3000
ctaaattagt ttctgacttc cgaaaagatt tccaattcta taaagtacgt gagattaaca 3060
attaccatca tgcccatgat gcgtatctaa atgccgtcgt tggaactgct ttgattaaga 3120
aatatccaaa acttgaatcg gagtttgtct atggtgatta taaagtttat gatgttcgta 3180
aaatgattgc taagtctgag caagaaatag gcaaagcaac cgcaaaatat ttcttttact 3240
ctaatatcat gaacttcttc aaaacagaaa ttacacttgc aaatggagag attcgcaaac 3300
gccctctaat cgaaactaat ggggaaactg gagaaattgt ctgggataaa gggcgagatt 3360
ttgccacagt gcgcaaagta ttgtccatgc cccaagtcaa tattgtcaag aaaacagaag 3420
tacagacagg cggattctcc aaggagtcaa ttttaccaaa aagaaattcg gacaagctta 3480
ttgctcgtaa aaaagactgg gatccaaaaa aatatggtgg ttttgatagt ccaacggtag 3540
cttattcagt cctagtggtt gctaaggtgg aaaaagggaa atcgaagaag ttaaaatccg 3600
ttaaagagtt actagggatc acaattatgg aaagaagttc ctttgaaaaa aatccgattg 3660
actttttaga agctaaagga tataaggaag ttaaaaaaga cttaatcatt aaactaccta 3720
aatatagtct tttgagttta gaaaacggtc gtaaacggat gctggctagt gccggagaat 3780
tacaaaaagg aaatgagctg gctctgccaa gcaaatatgt gaattttttta tatttagcta 3840 gtcattatga aaagttgaag ggtagtccag aagataacga acaaaaacaa ttgtttgtgg 3900
agcagcataa gcattattta gatgagatta ttgagcaaat cagtgaattt tctaagcgtg 3960
ttattttagc agatgccaat ttagataaag ttcttagtgc atataacaaa catagagaca 4020
aaccaatacg tgaacaagca gaaaatatta ttcatttatt tacgttgacg aatcttggag 4080
ctcccgctgc ttttaaatat tttgatacaa caattgatcg taaacgatat acgtctacaa 4140
aagaagtttt agatgccact cttatccatc aatccatcac tggtctttat gaaacacgca 4200
ttgatttgag tcagctagga ggtgactgac tcgagctaga ggcatcaaat aaaacgaaag 4260
gctcagtcga aagactgggc ctttcgtttt atctgttgtt tgtcggtgaa cgctctcctg 4320
agtaggacaa atccgccgcc ctagacctag caccctgcag ttgacagcta gctcagtcct 4380
aggtataatg ctagcttcca acggtttgat cgtcagtttt agagctagaa atagcaagtt 4440
aaaataaggc tagtccgtta tcaacttgaa aaagtggcac cgagtcggtg cttttttttct 4500 agatgatgat taaggatcta tttttttggg cggggccgcc caaaaaaat 4549

<210> SEQ ID NO 5
<211> LENGTH: 4549
<212> TYPE: DNA
<213> ORGANISM: Artificial Sequence
<220> FEATURE:
<223> OTHER INFORMATION: CRISPR/Cas9 system targeting blaSHV-18

<400> SEQUENCE: 5
tccctatcag tgatagagat tgacatccct atcagtgata gagatactga gcacatcagc 60
aggacgcact gaccgaattc attaaagagg agaaaggtgc ggccgcatgc atcaccatca 120
ccatcacatg gataagaaat actcaatagg cttagatatc ggcacaaata gcgtcggatg 180

-continued

```
ggcggtgatc actgatgaat ataaggttcc gtctgttcaa ggttctggga aatacagacc    240
gccacagtat caaaaaaaat cttatagggg ctcttttatt tgacagtgga gagacagcgg    300
aagcgactcg tctcaaacgg acagctcgta gaaggtatac acgtcggaag aatcgtattt    360
gttatctaca ggagattttt tcaaatgaga tggcgaaagt agatgatagt ttctttcatc    420
gacttgaaga gtcttttttg gtggaagaag acaagaagca tgaacgtcat cctatttttg    480
gaaatatagt agatgaagtt gcttatcatg agaaatatcc aactatctat catctgcgaa    540
aaaaattggt agattctact gataaagcgg atttgcgctt aatctatttg gccttagcgc    600
atatgattaa gtttcgtggt cattttttga ttgagggaga tttaaatcct gataatagtg    660
atgtggacaa actatttatc cagttggtac aaacctacaa tcaattattt gaagaaaacc    720
ctattaacgc aagtggagta gatgctaaag cgattctttc tgcacgattg agtaaatcaa    780
gacgattaga aaatctcatt gctcagctcc ccggtgagaa gaaaaatggc ttatttggga    840
atctcattgc tttgtcattg ggtttgaccc ctaattttaa atcaaatttt gatttggcag    900
aagatgctaa attacagctt tcaaaagata cttacgatga tgatttagat aatttattgg    960
cgcaaattgg agatcaatat gctgatttgt ttttggcagc taagaattta tcagatgcta   1020
ttttactttc agatatccta agagtaaata ctgaaataac taaggctccc ctatcagctt   1080
caatgattaa acgctacgat gaacatcatc aagacttgac tcttttaaaa gctttagttc   1140
gacaacaact tccagaaaag tataaagaaa tcttttttga tcaatcaaaa aacggatatg   1200
caggttatat tgatgggga gctagccaag aagaatttta taaatttatc aaaccaattt   1260
tagaaaaaat ggatggtact gaggaattat tggtgaaact aaatcgtgaa gatttgctgc   1320
gcaagcaacg gacctttgac aacggctcta ttccccatca aattcacttg ggtgagctgc   1380
atgctatttt gagaagacaa gaagactttt atccattttt aaaagacaat cgtgagaaga   1440
ttgaaaaaat cttgactttt cgaattcctt attatgttgg tccattggcg cgtggcaata   1500
gtcgttttgc atggatgact cggaagtctg aagaaacaat taccccatgg aattttgaag   1560
aagttgtcga taaaggtgct tcagctcaat catttattga acgcatgaca aactttgata   1620
aaaatcttcc aaatgaaaaa gtactaccaa aacatagttt gctttatgag tattttacgg   1680
tttataacga attgacaaag gtcaaatatg ttactgaagg aatgcgaaaa ccagcatttc   1740
tttcaggtga acagaagaaa gccattgttg atttactctt caaaacaaat cgaaaagtaa   1800
ccgttaagca attaaaagaa gattatttca aaaaaataga atgttttgat agtgttgaaa   1860
tttcaggagt tgaagataga tttaatgctt cattaggtac ctaccatgat ttgctaaaaa   1920
ttattaaaga taaagatttt ttggataatg aagaaaatga agatatctta gaggatattg   1980
ttttaacatt gaccttattt gaagataggg agatgattga ggaaagactt aaaacatatg   2040
ctcacctctt tgatgataag gtgatgaaac agcttaaacg tcgccgttat actggttggg   2100
gacgtttgtc tcgaaaattg attaatggta ttagggataa gcaatctggc aaaacaatat   2160
tagatttttt gaaatcagat ggttttgcca atcgcaattt tatgcagctg atccatgatg   2220
atagtttgac atttaaagaa gacattcaaa aagcacaagt gtctggacaa ggcgatagtt   2280
tacatgaaca tattgcaaat ttagctggta gccctgctat taaaaaaggt attttacaga   2340
ctgtaaaagt tgttgatgaa ttggtcaaag taatggggcg gcataagcca gaaaatatcg   2400
ttattgaaat ggcacgtgaa aatcagacaa ctcaaaaggg ccagaaaaat tcgcgagagc   2460
gtatgaaacg aatcgaagaa ggtatcaaag aattaggaag tcagattctt aaagagcatc   2520
ctgttgaaaa tactcaattg caaaatgaaa agctctatct ctattatctc caaaatggaa   2580
```

```
gagacatgta tgtggaccaa gaattagata ttaatcgttt aagtgattat gatgtcgatc   2640
acattgttcc acaaagtttc cttaaagacg attcaataga caataaggtc ttaacgcgtt   2700
ctgataaaaa tcgtggtaaa tcggataacg ttccaagtga agaagtagtc aaaaagatga   2760
aaaactattg gagacaactt ctaaacgcca agttaatcac tcaacgtaag tttgataatt   2820
taacgaaagc tgaacgtgga ggtttgagtg aacttgataa agctggtttt atcaaacgcc   2880
aattggttga aactcgccaa atcactaagc atgtggcaca aattttggat agtcgcatga   2940
atactaaata cgatgaaaat gataaactta ttcgagaggt taaagtgatt accttaaaat   3000
ctaaattagt ttctgacttc cgaaaagatt tccaattcta taaagtacgt gagattaaca   3060
attaccatca tgcccatgat gcgtatctaa atgccgtcgt tggaactgct ttgattaaga   3120
aatatccaaa acttgaatcg gagtttgtct atggtgatta taaagtttat gatgttcgta   3180
aaatgattgc taagtctgag caagaaatag gcaaagcaac cgcaaaatat ttcttttact   3240
ctaatatcat gaacttcttc aaaacagaaa ttacacttgc aaatggagag attcgcaaac   3300
gccctctaat cgaaactaat ggggaaactg gagaaattgt ctgggataaa gggcgagatt   3360
ttgccacagt gcgcaaagta ttgtccatgc cccaagtcaa tattgtcaag aaaacagaag   3420
tacagacagg cggattctcc aaggagtcaa ttttaccaaa aagaaattcg gacaagctta   3480
ttgctcgtaa aaaagactgg gatccaaaaa aatatggtgg ttttgatagt ccaacggtag   3540
cttattcagt cctagtggtt gctaaggtgg aaaaagggaa atcgaagaag ttaaaatccg   3600
ttaaagagtt actagggatc acaattatgg aaagaagttc ctttgaaaaa aatccgattg   3660
actttttaga agctaaagga tataaggaag ttaaaaaaga cttaatcatt aaactaccta   3720
aatatagtct ttttgagtta gaaaacggtc gtaaacggat gctggctagt gccggagaat   3780
tacaaaaagg aaatgagctg gctctgccaa gcaaatatgt gaattttttta tatttagcta   3840
gtcattatga aaagttgaag ggtagtccag aagataacga acaaaaacaa ttgtttgtgg   3900
agcagcataa gcattattta gatgagatta ttgagcaaat cagtgaattt tctaagcgtg   3960
ttattttagc agatgccaat ttagataaag ttcttagtgc atataacaaa catagagaca   4020
aaccaatacg tgaacaagca gaaaatatta ttcatttatt tacgttgacg aatcttggag   4080
ctcccgctgc ttttaaatat tttgatacaa caattgatcg taaacgatat acgtctacaa   4140
aagaagtttt agatgccact cttatccatc aatccatcac tggtctttat gaaacacgca   4200
ttgatttgag tcagctagga ggtgactgac tcgagctaga ggcatcaaat aaaacgaaag   4260
gctcagtcga aagactgggc ctttcgtttt atctgttgtt tgtcggtgaa cgctctcctg   4320
agtaggacaa atccgccgcc ctagacctag caccctgcag ttgacagcta gctcagtcct   4380
aggtataatg ctagcctaag cgaaagccag ctgtcgtttt agagctagaa atagcaagtt   4440
aaaataaggc tagtccgtta tcaacttgaa aaagtggcac cgagtcggtg cttttttttct   4500
agatgatgat taaggatcta tttttttggg cggggccgcc caaaaaaat                4549
```

<210> SEQ ID NO 6
<211> LENGTH: 12
<212> TYPE: DNA
<213> ORGANISM: Artificial Sequence
<220> FEATURE:
<223> OTHER INFORMATION: vanC-2-targetting peptide nucleic acid sequence

<400> SEQUENCE: 6

```
atgtttttct tc                                                        12
```

<210> SEQ ID NO 7
<211> LENGTH: 12
<212> TYPE: DNA
<213> ORGANISM: Artificial Sequence
<220> FEATURE:
<223> OTHER INFORMATION: C. albicans ITS2-targetting antisense
oligonucleotide sequence 1

<400> SEQUENCE: 7
ccattgtcaa ag 12

<210> SEQ ID NO 8
<211> LENGTH: 12
<212> TYPE: DNA
<213> ORGANISM: Artificial Sequence
<220> FEATURE:
<223> OTHER INFORMATION: C. tropicalis ITS2-targetting antisense
oligonucleotide sequence 2

<400> SEQUENCE: 8
tcgcttaaaa ta 12

<210> SEQ ID NO 9
<211> LENGTH: 12
<212> TYPE: DNA
<213> ORGANISM: Artificial Sequence
<220> FEATURE:
<223> OTHER INFORMATION: C. parapsilosis ITS2-targetting antisense
oligonucleotide sequence 3

<400> SEQUENCE: 9
aaacccgagg gt 12

<210> SEQ ID NO 10
<211> LENGTH: 10
<212> TYPE: PRT
<213> ORGANISM: Artificial Sequence
<220> FEATURE:
<223> OTHER INFORMATION: Penetration peptide

<400> SEQUENCE: 10

Lys Phe Phe Lys Phe Phe Lys Phe Phe Lys
1 5 10

<210> SEQ ID NO 11
<211> LENGTH: 1020
<212> TYPE: DNA
<213> ORGANISM: Escherichia coli
<220> FEATURE:
<221> NAME/KEY: gene
<222> LOCATION: (1)..(1020)
<223> OTHER INFORMATION: blaKPC-3

<400> SEQUENCE: 11
agctgtagcg gcctgattac atccggccgc tacacctagc tccaccttca aacaaggaat 60
atcgttgatg tcactgtatc gccgtctagt tctgctgtct tgtctctcat ggccgctggc 120
tggcttttct gccaccgcgc tgaccaacct cgtcgcggaa ccattcgcta aactcgaaca 180
ggactttggc ggctccatcg gtgtgtacgc gatggatacc ggctcaggcg caactgtaag 240
ttaccgcgct gaggagcgct tcccactgtg cagctcattc aagggctttc ttgctgccgc 300
tgtgctggct cgcagccagc agcaggccgg cttgctggac acacccatcc gttacggcaa 360
aaatgcgctg gttccgtggt cacccatctc ggaaaaatat ctgacaacag gcatgacggt 420
ggcggagctg tccgcggccg ccgtgcaata cagtgataac gccgccgcca atttgttgct 480

-continued

```
gaaggagttg ggcggcccgg ccgggctgac ggccttcatg cgctctatcg gcgataccac     540

gttccgtctg gaccgctggg agctggagct gaactccgcc atcccaggcg atgcgcgcga     600

tacctcatcg ccgcgcgccg tgacggaaag cttacaaaaa ctgacactgg gctctgcact     660

ggctgcgccg cagcggcagc agtttgttga ttggctaaag ggaaacacga ccggcaacca     720

ccgcatccgc gcggcggtgc cggcagactg ggcagtcgga gacaaaaccg gaacctgcgg     780

agtgtatggc acggcaaatg actatgccgt cgtctggccc actgggcgcg cacctattgt     840

gttggccgtc tacacccggg cgcctaacaa ggatgacaag tacagcgagg ccgtcatcgc     900

cgctgcggct agactcgcgc tcgagggatt gggcgtcaac gggcagtaag gctctgaaaa     960

tcatctattg gcccaccacc gccgcccttg cgggcggcat ggattaccaa ccactgtcac    1020
```

<210> SEQ ID NO 12
<211> LENGTH: 1020
<212> TYPE: DNA
<213> ORGANISM: Escherichia coli
<220> FEATURE:
<221> NAME/KEY: gene
<222> LOCATION: (1)..(1020)
<223> OTHER INFORMATION: blaNDM-1

<400> SEQUENCE: 12

```
aaagcccagc ttcgcataaa acgcctctgt cacatcgaaa tcgcgcgatg gcagattggg      60

ggtgacgtgg tcagccatgg ctcagcgcag cttgtcggcc atgcgggccg tatgagtgat     120

tgcggcgcgg ctatcggggg cggaatggct catcacgatc atgctggcct tggggaacgc     180

cgcaccaaac gcgcgcgctg acgcggcgta gtgctcagtg tcggcatcac cgagattgcc     240

gagcgacttg gccttgctgt ccttgatcag gcagccacca aaagcgatgt cggtgccgtc     300

gatcccaacg gtgatattgt cactggtgtg gccggggccg gggtaaaata ccttgagcgg     360

gccaaagttg ggcgcggttg ctggttcgac ccagccattg gcggcgaaag tcaggctgtg     420

ttgcgccgca accatcccct cttgcggggc aagctggttc gacaacgcat tggcataagt     480

cgcaatcccc gccgcatgca gcgcgtccat accgcccatc ttgtcctgat gcgcgtgagt     540

caccaccgcc agcgcgaccg gcaggttgat ctcctgcttg atccagttga ggatctgggc     600

ggtctggtca tcggtccagg cggtatcgac caccagcacg cggccgccat ccctgacgat     660

caaaccgttg gaagcgactg ccccgaaacc cggcatgtcg agataggaag tgtgctgcca     720

gacattcggt gcgagctggc ggaaaaccag atcgccaaac cgttggtcgc cagtttccat     780

ttgctggcca atcgtcgggc ggatttcacc gggcatgcac ccgctcagca tcaatgcagc     840

ggctaatgcg gtgctcagct tcgcgaccgg gtgcataata ttgggcaatt ccatcaagtt     900

ttccttttat tcagcattaa aaaccccgca aatgcgaggc ctagtaaata gatgatctta     960

atttggttca ctgtagcaaa aatatggggc gaattcaaac atgaggtgcg acagtttcaa    1020
```

<210> SEQ ID NO 13
<211> LENGTH: 983
<212> TYPE: DNA
<213> ORGANISM: Escherichia coli
<220> FEATURE:
<221> NAME/KEY: gene
<222> LOCATION: (1)..(983)
<223> OTHER INFORMATION: blaSHV-18

<400> SEQUENCE: 13

```
ttgtgaatca gcaaaacgcc gggttattct tatttgtcgc ttctttactc gcctttatcg      60

gccctcactc aaggatgtat tgtggttatg cgttattttc gcctgtgtat tatctccctg     120
```

-continued

```
ttagccaccc tgccgctggc ggtacacgcc agcccgcagc cgcttgagca aattaaacta    180

agcgaaagcc agctgtcggg cagcgtaggc atgatagaaa tggatctggc cagcggccgc    240

acgctgaccg cctggcgcgc cgatgaacgc tttcccatga tgagcacctt taaagtagtg    300

ctctgcggcg cagtgctggc gcgggtggat gccggtgacg aacagctgga gcgaaagatc    360

cactatcgcc agcaggatct ggtggactac tcgccggtca gcgaaaaaca ccttgccgac    420

ggcatgacgg tcggcgaact ctgtgccgcc gccattacca tgagcgataa cagcgccgcc    480

aatctgctgc tggccaccgt cggcggcccc gcaggattga ctgccttttt gcgccagatc    540

ggcgacaacg tcacccgcct tgaccgctgg gaaacggaac tgaatgaggc gcttcccggc    600

gacgcccgcg acaccactac cccggccagc atggccgcga ccctgcgcaa gctgctgacc    660

agccagcgtc tgagcgcccg ttcgcaacgg cagctgctgc agtggatggt ggacgatcgg    720

gtcgccggac cgttgatccg ctccgtgctg ccggcgggct ggtttatcgc cgataagacc    780

ggagctgcca aacggggtgc gcgcgggatt gtcgccctgc ttggcccgaa taacaaagca    840

gagcggattg tggtgattta tctgcgggat acgccggcga gcatggccga gcgaaatcag    900

caaatcgccg ggatcggcgc ggcgctgatc gagcactggc aacgctaacc cggcggtggc    960

cgcgcgcgtt atccggctcg tag                                            983


<210> SEQ ID NO 14
<211> LENGTH: 1200
<212> TYPE: DNA
<213> ORGANISM: Enterococcus casseliflavus
<220> FEATURE:
<221> NAME/KEY: gene
<222> LOCATION: (1)..(1200)
<223> OTHER INFORMATION: vanC-2

<400> SEQUENCE: 14

gactgaatgt agtaagaatc gaaaagcgga aggaagaaaa acatgaaaaa aatcgccatt     60

atttttggag gcaattcacc ggaatacacc gtttctttag cttcagcaac tagcgcaatc    120

gaagcactcc aatcatctcc ctatgactac gacctctctt tgatcgggat cgccccagat    180

gctatggatt ggtacttgta tacaggagaa ctggaaaaca tccgacaaga cacgtggttg    240

ttggatacga aacataaaca gaaaatacag ccgctattcg aaggaaacgg cttttggcta    300

agtgaagagc agcaaacgtt ggtacctgat gttttatttc ccattatgca tggcaaatac    360

ggggaagatg gcagtatcca aggattgttt gaattgatga agctgcctta tgtaggctgc    420

ggggtggcaa gttctgcctt atgtatgaac aaatggctgc tgcatcaagc tgcagcagcc    480

attggcgtac aaagtgctcc tacgattctc ttgacaaatc aagccaacca gcaagaacaa    540

atcgaagctt ttatccagac ccatggcttt ccagttttct ttaagcctaa tgaagcgggc    600

tcctcaaaag ggatcactaa agtcacctgc gttgaagaaa tcgcttctgc cttaaaagaa    660

gcctttactt attgttccgc agtgctccta caaaaaaata ttgtcggtgt tgagatcggt    720

tgcggtattt tgggcaacga ctctttgact gtcggtgctt gtgacgccat ttcattagaa    780

gacggctttt tcgattttga agaaaagtac cagctgatca gcgccaaaat caccgtccct    840

gcgccattgc ctgaaacgat tgaaaccaag gtcaaagaac aagctcagct gctctatcgt    900

agtcttggtc ttaaaggtct tgctcgcatc gattttttttg tcacggatca aggagaacta    960

tacctgaatg aaatcaatac tatgccgggc tttacgagtc actcccgcta tcctgccatg   1020

atggcagcgg tcggcttatc ctatcaagaa ctactacaaa aactgcttat cttagcaaag   1080
```

-continued

```
gaggaagtca aatgaatccc tatctacagt tagttagcaa aaaatttccg ttagaaaaaa   1140

accaagaacc ccctcattta gtccttgctg ccttcagcga agacgaggtt tacttgcagc   1200
```

SEQUENCE-SPECIFIC DETECTION AND PHENOTYPE DETERMINATION

CROSS REFERENCE TO RELATED APPLICATIONS

This application is a divisional of U.S. patent application Ser. No. 15/136,646, filed on Apr. 22, 2016, which claims the benefit of priority of U.S. Provisional Patent Application No. 62/155,011, filed Apr. 30, 2015, and is related to U.S. patent application Ser. No. 14/550,335, filed Nov. 21, 2014; the entire disclosures of all are hereby incorporated by reference, in their entireties, for all purposes.

REFERENCE TO SEQUENCE LISTING

This application contains a Sequence Listing submitted as an electronic text file named "33171_US1.txt", having a size in bytes of 20 kb, and created on Mar. 25, 2016. The information contained in this electronic file is hereby incorporated by reference in its entirety pursuant to 37 CFR § 1.52(e)(5).

BACKGROUND OF THE INVENTION

Cell-reporter systems can exhibit cross-reactivity and microbial interference with non-target organisms. For example, if an Enterobacteriaceae reporter is used to detect *E. coli* in a stool sample; other species of Enterobacteriaceae such as *K. pneumoniae* may produce a cross-reactive signal resulting in a false positive result. Furthermore, species of other Family of bacteria, such as *P. aeruginosa, A. baumannii*, and *S. maltophilia*, which may be present in a sample, may result in microbial interference resulting in a false negative result.

Antimicrobial susceptibility tests (AST) measure the response of a microorganism to an antimicrobial and are used to determine if the microorganism is susceptible or non-susceptible to the antimicrobial. The response of a microorganism to an antimicrobial may be due to a variety of mechanisms, all of which give the same response or phenotype. For example, in carbapenem resistant Enterobacteriaceae (CRE), resistance to carbapenem antibiotics may be due to a variety of carbapenemases encoded by different genes and gene variants including $bla_{NDM\text{-}1}$, $bla_{KPC}$, $bla_{IMP}$, $bla_{VIM}$, $bla_{CMY}$, etc. as well as situations that result in a carbapenem non-susceptible phenotype despite the lack of a carbapenemase such as non-carbapenemase β-lactamase hyper-expression and mutations that result in decreased uptake of a carbapenem into a cell (e.g. porin mutations).

AST is not capable of discriminating between different resistance mechanisms that impart a common phenotypic response. When testing the response of an Enterobacteriaceae to meropenem, for example, if it is found that the Enterobacteriaceae is resistant to meropenem, it cannot be determined from this assay if the resistance is due to $bla_{NDM\text{-}1}$ or $bla_{KPC}$, or other carbapenem resistance mechanisms.

Extensions of AST have been developed to provide limited information about the mechanism that imparts a resistance phenotype in a microorganism. For example, when conducting AST testing on Enterobacteriaceae using Amoxicillin, if the organism is found to be resistant to Amoxicillin but susceptible to Amoxicillin in the presence of clavulanic acid, a β-lactamase inhibitor, this result can indicate that a β-lactamase is linked to the Amoxicillin-resistance phenotype. However, this technique only informs of the role of a β-lactamase but not the identity of the specific β-lactamase.

Nucleic acid amplification techniques such as polymerase chain reaction (PCR) can be employed to determine the presence of specific genes that may impart a resistance phenotype in an organism. However, these techniques cannot distinguish between viable and non-viable organisms leading to possible false-positive results and also cannot determine if the detected gene is expressed and are thus incapable of measuring the phenotypic response of an organism to an antimicrobial and thus cannot generally determine antimicrobial susceptibility.

Due to these limitations, there is a need for a means of determining the underlying mechanism that imparts a phenotypic response in an organism. The identity of the specific underlying mechanism that imparts a given phenotype can be important information for epidemiological analysis and other related analyses.

SUMMARY OF THE INVENTION

Disclosed herein is a method for determining a mechanism for an antimicrobial susceptibility phenotype, comprising: obtaining a sample comprising at least one microorganism that is not susceptible to at least one antimicrobial agent; contacting the sample with the antimicrobial agent, wherein the antimicrobial agent can kill, inhibit the growth, or otherwise compromise the viability of one or more microorganisms; contacting the sample with at least one compound comprising an oligonucleotide molecule targeting at least one specific nucleic acid sequence that is involved in a non-susceptible phenotype to the antimicrobial agent, optionally wherein the oligonucleotide molecule inhibits the nucleic acid sequence; and determining the mechanism for the antimicrobial susceptibility phenotype of the microorganism based on the presence or absence of a detectable indication of viability associated with the microorganism when the microorganism is in contact with the antimicrobial agent and the oligonucleotide molecule, wherein the presence of the detectable indication of viability indicates that the specific nucleic acid sequence targeted by the oligonucleotide molecule is not related to the mechanism for the antimicrobial susceptibility phenotype to the antimicrobial agent, and wherein the absence of the detectable indication of viability indicates that the specific nucleic acid sequence targeted by the oligonucleotide molecule is related to the mechanism for the antimicrobial susceptibility phenotype to the antimicrobial agent. Other methods, compositions, systems, cultures, molecules, and kits are similarly described herein.

In some aspects, the compound is a PNA (peptide nucleic acid). In some aspects, the compound is a peptide—PNA. In some aspects, the peptide facilitates uptake of the oligonucleotide molecule into the microorganism. In some aspects, the PNA targets a translation initiation region (TIR) of a gene. In some aspects, the peptide—PNA targets a β-lactam resistance gene or a vancomycin resistance gene. In some aspects, the peptide—PNA targets a $bla_{KPC\text{-}3}$ gene, a $bla_{NDM\text{-}1}$ gene, a $bla_{SHV\text{-}18}$ gene, a vanC gene.

In some aspects, contacting the sample with at least one compound comprising an oligonucleotide molecule comprises introducing into the microorganism a vector comprising the oligonucleotide molecule.

In some aspects, the oligonucleotide molecule is a CRISPR RNA (crRNA). In some aspects, the crRNA is expressed from a CRISPR/Cas system within the microorganism. In some aspects, the crRNA targets a $bla_{NDM-1}$ gene or a $bla_{SHV-18}$ gene or transcript.

In some aspects, the oligonucleotide molecule is an antisense oligonucleotide.

In some aspects, the compound is a double-stranded RNA (dsRNA) comprising a sense strand and an antisense strand, wherein the antisense strand comprises the antisense molecule. In some aspects, each strand of the dsRNA is 8 to 49 nucleotides in length (e.g., 8, 9, 10, 11, 12, 13, 14, 15, 16, 17, 18, 19, 20, 21, 22, 23, 24, 25, 26, 27, 28, 29, or 30 nucleotides in length), and optionally wherein each strand comprises a 3' T or TT. In some aspects, at least one of the strands comprises at least one chemically modified nucleotide. In some aspects, the chemically modified nucleotide is a 2'-modified nucleotide. In some aspects, the 2'-modified nucleotide is a 2'-methyl substituted nucleotide or a 2'-amino substituted nucleotide.

In some aspects, the specific nucleic acid sequence is a DNA sequence or an mRNA sequence.

In some aspects, the presence of the detectable indication of viability indicates that the microorganism is viable. In some aspects, the absence of the detectable indication of viability indicates that the microorganism is not viable.

In some aspects, a method disclosed herein further comprises contacting the sample with a second compound comprising an oligonucleotide molecule targeting a second specific nucleic acid sequence involved with antimicrobial non-susceptibility to the antimicrobial agent in the microorganism.

In some aspects, the microorganism is a prokaryote or a eukaryote.

In some aspects, the detectable indication of viability is growth of the microorganism, a marker associated with the microorganism, or a detectable signal associated with the microorganism.

In some aspects, a method disclosed herein further comprises contacting the sample with a reporter nucleic acid molecule encoding a reporter molecule, under conditions such that the reporter molecule enters the microorganism and provides the detectable indication of viability. In some aspects, the reporter system is a liposome-based reporter system, a phage-based reporter system, or a non-replicative transduction particle-based reporter system.

In some aspects, the at least one microorganism comprises a reporter nucleic acid molecule encoding a reporter molecule.

In some aspects, a method disclosed herein further comprises contacting the sample with a non-replicative transduction particle (NRTP) comprising a reporter nucleic acid molecule encoding a reporter molecule, under conditions such that the NRTP inserts into the microorganism the reporter nucleic acid molecule and such that the reporter molecule provides the detectable indication of viability.

In some aspects, the reporter nucleic acid molecule is a gene encoding a light-emitting molecule. In some aspects, the gene is a luciferase gene.

In some aspects, detecting the detectable indication of viability comprises detecting a presence or absence of the reporter molecule. In some aspects, detecting the detectable indication of viability comprises detecting a presence or absence of a reaction mediated by the reporter molecule. In other aspects, detecting the detectable indication of viability comprises detecting a conformation, activity, or other characteristic of the reporter molecule (e.g., fluorescence or ability to bind to or otherwise interact with another molecule).

In some aspects, the microorganism is of the family Enterobacteriaceae, the genus *Enterococcus*, or the genus *Candida.*

In some aspects, the microorganism is of the genus *Escherichia, Mycobacterium, Staphylococcus, Listeria, Clostridium, Streptococcus, Helicobacter, Rickettsia, Haemophilus, Xenorbabdus, Acinetobacter, Bordetella, Pseudomonas, Aeromonas, Actinobacillus, Pasteurella, Vibrio, Legionella, Bacillus, Calothrix, Methanococcus, Stenotrophomonas, Chlamydia, Neisseria, Salmonella, Shigella, Campylobacter* or *Yersinia.*

In some aspects, the antimicrobial is a β-lactam or vancomycin.

In some aspects, the antimicrobial agent is of the group or class Penicillins, Cephalosporin, Carbapenems, Aminoglycosides, Fluoroquinolone, Lincosamide, Polymyxin, Tetracycline, Macrolide, Oxazolidinone, Streptogramins, Rifamycin, or Glycopeptide.

In some aspects, the antimicrobial is Ampicillin, Ampicillin-sulbactam, Pipercillin-tazobactam, Oxacillin, Penicillin, Cefazolin, Cefepime, Cefotaxime, Ceftazidime, Ceftriaxone, Ceftaroline fosomil, Ertapenem, Imipenem, Meropenem, Amikacin, Gentamicin, Gentamicin Synergy, Streptomycin Synergy, Tobramycin, Ciprofloxacin, Levofloxacin, Clindamycin, Colistin, Daptomycin, Doxycycline, Erythromycin, Linezolid, Nitrofurantoin, Quinupristin-dalfopristin, Rifampin, Tigecycline, Trimethoprim-sulfamethoxazole, fosfomycin, cefoxitin, tetracycline, moxifloxacin, or tedizolid.

In some aspects, detecting the detectable indication of viability comprises observing the growth of the microorganism, optionally wherein growth is observed using cell culture.

In some aspects, the compound further comprises a liposome.

In some aspects, the sample is contacted with the antimicrobial agent prior to contacting the sample with the compound.

In some aspects, the sample is contacted with the compound prior to contacting the sample with the antimicrobial agent, or wherein the sample is contacted with the compound and the agent simultaneously.

In some aspects, the sample, compound, and a reporter nucleic acid are contacted with each other in any sequential permutation or simultaneously.

Also disclosed herein is a method for determining a mechanism for an antimicrobial susceptibility phenotype, comprising: obtaining a sample comprising at least one microorganism that is not susceptible to at least one antimicrobial agent, and wherein the sample further comprises: the antimicrobial agent, wherein the antimicrobial agent can kill, inhibit the growth, or otherwise compromise the viability of one or more microorganisms; and at least one compound comprising an oligonucleotide molecule targeting at least one specific nucleic acid sequence that is involved with a non-susceptible phenotype to the antimicrobial agent; and determining the mechanism for the non-susceptible phenotype for the microorganism based on the presence or absence of a detectable indication of viability associated with the microorganism when the microorganism is in contact with the antimicrobial agent and the oligonucleotide molecule, wherein the presence of the detectable indication of viability indicates that the specific nucleic acid sequence targeted by the oligonucleotide molecule is not related to the mechanism for the non-susceptible phenotype to the antimicrobial agent, and wherein the absence of the detectable indication of viability indicates that the specific nucleic acid sequence targeted by the oligonucleotide molecule is related to the mechanism for the non-susceptible phenotype to the antimicrobial agent.

Also disclosed herein is an isolated microorganism that is not susceptible to at least one antimicrobial agent comprising: the antimicrobial agent, wherein the antimicrobial agent can kill, inhibit the growth, or otherwise compromise the viability of one or more microorganisms; at least one compound comprising an oligonucleotide molecule targeting at least one specific nucleic acid sequence that is involved with a non-susceptible phenotype to the antimicrobial agent; and a reporter, optionally wherein the reporter is a marker, a detectable signal, a reporter nucleic acid molecule encoding a reporter molecule, or a non-replicative transduction particle (NRTP) comprising a reporter nucleic acid molecule encoding a reporter molecule.

Also disclosed herein is a method of producing a microorganism disclosed herein, comprising: contacting the microorganism with an antimicrobial agent; contacting the microorganism with a compound comprising an oligonucleotide molecule; and contacting the microorganism with a reporter.

Also disclosed herein is an in vitro cell culture comprising a microorganism that is not susceptible to at least one antimicrobial agent, and further comprising: the antimicrobial agent, wherein the antimicrobial agent can kill, inhibit the growth, or otherwise compromise the viability of one or more microorganisms; at least one compound comprising an oligonucleotide molecule targeting at least one specific nucleic acid sequence that is involved with a non-susceptible phenotype to the antimicrobial agent; and a reporter, optionally wherein the reporter is a marker, a detectable signal, a reporter nucleic acid molecule encoding a reporter molecule, or a non-replicative transduction particle (NRTP) comprising a reporter nucleic acid molecule encoding a reporter molecule.

Also disclosed herein is a method of producing a cell culture, comprising contacting the culture with an antimicrobial agent; contacting the culture with a compound comprising an oligonucleotide molecule; and contacting the culture with a reporter.

Also disclosed herein is a peptide nucleic acid (PNA) molecule for inhibiting the expression of a gene involved with carbapenem non-susceptibility in Enterobacteriaceae, the PNA molecule comprising the nucleotide sequence of SEQ ID NO: 2 or SEQ ID NO: 3.

Also disclosed herein is an PNA molecule for inhibiting the expression of a gene involved with vancomycin non-susceptibility in *Enterococcus*, the PNA molecule comprising the nucleotide sequence of SEQ ID NO: 6.

Also disclosed herein is an antisense molecule for inhibiting the expression of an internal transcribed spacer region in *Candida*, the antisense molecule comprising the nucleotide sequence of SEQ ID NO: 7, SEQ ID NO: 8, or SEQ ID NO: 9.

Also disclosed herein is a kit for determining a mechanism for a non-susceptible phenotype for a microorganism that is not susceptible to an antimicrobial agent, comprising: an antimicrobial agent, wherein the antimicrobial agent can kill, inhibit the growth, or otherwise compromises the viability of one or more microorganisms; a compound comprising an oligonucleotide molecule targeting a specific nucleic acid sequence that is involved with a non-susceptible phenotype to the antimicrobial agent; and instructions for using the antimicrobial agent and the oligonucleotide molecule to determine the mechanism for the non-susceptible phenotype for the microorganism that is not susceptible to the antimicrobial agent based on the presence or absence of a detectable indication of viability associated with the microorganism when the microorganism is in contact with the antimicrobial agent and the oligonucleotide molecule, wherein the presence of the detectable indication of viability indicates that the specific nucleic acid sequence targeted by the oligonucleotide molecule is not related to the mechanism for the non-susceptible phenotype to the antimicrobial agent, and wherein the absence of the detectable indication of viability indicates that the specific nucleic acid sequence targeted by the oligonucleotide molecule is related to the mechanism for the non-susceptible phenotype to the antimicrobial agent.

Also disclosed herein is a method for determining a mechanism involved in a non-susceptible phenotype, comprising: obtaining a sample comprising an Enterobacteriaceae that is not susceptible to carbapenem; contacting the sample with carbapenem; contacting the sample with an oligonucleotide molecule that targets a gene associated with carbapenem resistance; and determining the mechanism of carbapenem non-susceptibility for the Enterobacteriaceae based on the presence or absence of a detectable indication of viability associated with the Enterobacteriaceae when the Enterobacteriaceae is in contact with the carbapenem and the oligonucleotide molecule, wherein the presence of the detectable indication of viability indicates that the gene targeted by the oligonucleotide molecule is not related to the mechanism of carbapenem non-susceptibility, and wherein the absence of the detectable indication of viability indicates that the gene targeted by the oligonucleotide molecule is related to the mechanism of carbapenem non-susceptibility.

Also disclosed herein is a method for determining the presence of an organism of interest, comprising: obtaining a sample potentially comprising at least one organism of interest; contacting the sample with at least one compound comprising an oligonucleotide molecule targeting at least one specific nucleic acid sequence that is involved with the viability of the organism, wherein the specific nucleic acid sequence is unique to the organism; and determining the presence of the organism based on the presence or absence of a detectable indication of viability associated with the organism when the organism is in contact with the oligonucleotide molecule, wherein the presence of the detectable indication of viability indicates that the organism of interest is not present in the sample, and wherein the absence of the detectable indication of viability indicates that the organism of interest may be present in the sample Also disclosed herein is a method for determining a presence of an organism of interest, comprising: obtaining a sample potentially comprising at least one organism of interest and at least one compound comprising an oligonucleotide molecule targeting at least one specific nucleic acid sequence that is involved with the viability of the organism, wherein the specific nucleic acid sequence is unique to the organism; and determining the presence of the organism based on the presence or absence of a detectable indication of viability associated with the organism when the organism is in contact with the oligonucleotide molecule, wherein the presence of the detectable indication of viability indicates that the organism of interest is not present in the sample, and wherein the absence of the detectable indication of viability indicates that the organism of interest may be present in the sample.

Also disclosed herein is an isolated organism comprising: at least one compound comprising an oligonucleotide molecule targeting at least one specific nucleic acid sequence that is involved with the viability of the organism, wherein the specific nucleic acid sequence is unique to the organism; and a reporter, optionally wherein the reporter is a marker, a detectable signal, a reporter nucleic acid molecule encoding a reporter molecule, or a non-replicative transduction particle (NRTP) comprising a reporter nucleic acid molecule encoding a reporter molecule.

Also disclosed herein is a method of producing an isolated organism, comprising: contacting the organism with a compound comprising an oligonucleotide molecule; and contacting the organism with a reporter.

Also disclosed herein is an in vitro cell culture comprising an organism and further comprising: at least one compound comprising an oligonucleotide molecule targeting at least one specific nucleic acid sequence that is involved with the viability of the organism, wherein the specific nucleic acid sequence is unique to the organism; and a reporter, optionally wherein the reporter is a marker, a detectable signal, a reporter nucleic acid molecule encoding a reporter molecule, or a non-replicative transduction particle (NRTP) comprising a reporter nucleic acid molecule encoding a reporter molecule.

Also disclosed herein is a method of producing an in vitro cell culture, comprising: contacting the culture with a compound comprising an oligonucleotide molecule; and contacting the culture with a reporter.

Also disclosed herein is a kit for determining the presence of an organism of interest, comprising: a compound comprising an oligonucleotide molecule targeting a specific nucleic acid sequence that is involved with the viability of the organism, wherein the specific nucleic acid sequence is unique to the organism; and instructions for using the oligonucleotide molecule to determine the presence of the organism based on the presence or absence of a detectable indication of viability associated with the organism when the organism is in contact with the oligonucleotide molecule, wherein the presence of the detectable indication of viability indicates that the organism of interest is not present in the sample, and wherein the absence of the detectable indication of viability indicates that the organism of interest may be present in the sample.

Also disclosed herein is a method for determining the presence of an organism of interest, comprising: obtaining a sample potentially comprising at least one organism of interest; contacting a first portion of the sample with at least one compound comprising an oligonucleotide molecule targeting at least one specific nucleic acid sequence that is involved with the viability of the organism, wherein the specific nucleic acid sequence is unique to the organism; determining the presence of the organism in the first portion of the sample based on the presence or absence of a detectable indication of viability associated with the organism when the organism is in contact with the oligonucleotide molecule, wherein the presence of the detectable indication of viability indicates that the organism of interest is not present in the sample, and wherein the absence of the detectable indication of viability indicates that the organism of interest may be present in the sample; and determining the presence of the organism in a second portion of the sample that does not contain the oligonucleotide molecule based on the presence or absence of a detectable indication of viability associated with the organism, wherein the presence of the detectable indication of viability indicates that the organism of interest may be present in the sample, and wherein the absence of the detectable indication of viability indicates that the organism of interest is not present in the sample.

Also disclosed herein is a method for reducing the amount of potentially cross-reactive or interfering organisms in an assay designed to detect a target organism, comprising: obtaining a sample potentially comprising at least one organism that is potentially cross-reactive or interfering in an assay designed to detect a target organism; contacting the cross-reactive or interfering organism with at least one compound comprising an oligonucleotide molecule targeting at least one specific nucleic acid sequence that is involved with the viability of the potentially cross-reactive or interfering organism, wherein the specific nucleic acid sequence is unique to the organism; and causing the organism to lose viability.

BRIEF DESCRIPTION OF THE DRAWINGS

These and other features, aspects, and advantages of the present disclosure will become better understood with regard to the following description, and accompanying drawings, where:

FIG. 5 depicts an example of results of a peptide PNA cell-reporter AST assay where + indicates that the reporter assay produced a positive result and – indicates that the reporter assay produced a negative result.

FIG. 6 depicts an example of results of a CRISPR Cas9 cell-reporter AST assay where + indicates that the reporter assay produced a positive result and – indicates that the reporter assay produced a negative result.

FIG. 7 depicts an example of results of a VRE cell-reporter assay where + indicates that the reporter assay produced a positive result and – indicates that the reporter assay produced a negative result.

FIG. 8 includes a list of ITS2 sequences that can be used for producing 2'-OMe modified antisense oligonucleotides (AON) targeting each species.

FIG. 9 depicts an assay setup for the combination of AON used for *Candida* spp. identification.

DETAILED DESCRIPTION OF THE INVENTION

Figure 1:
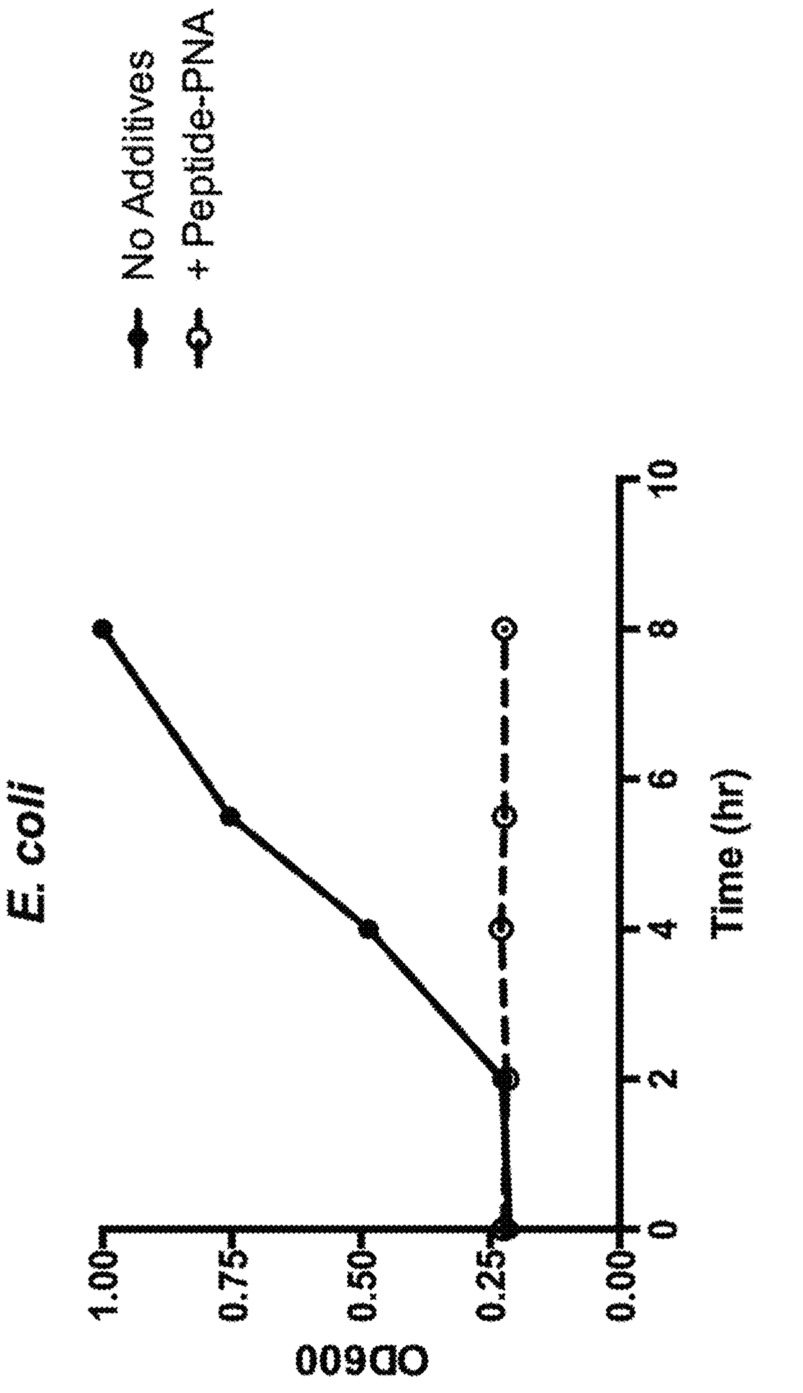
FIG. 1 shows the effect of *E. coli*-specific peptide-PNA on the growth of *E. coli.*

Terms used in the claims and specification are defined as set forth below unless otherwise specified.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

A "reporter molecule" or "reporter" refers to a molecule (e.g., nucleic acid-derived or amino acid-derived) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell. The reporter molecule can also be used to indicate the viability of a cell. Alternatively, the reporter molecule can be a nucleic acid, such as an aptamer or ribozyme.

In some aspects, the reporter nucleic acid molecule is operatively linked to a promoter. In other aspects, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged (e.g., as concatameric DNA) into a progeny virus during virus replication. In other aspects, the reporter nucleic acid molecule includes factors that influence the transcription or translation of the reporter gene (e.g., specific ribosome binding sites, codon usage) that can similarly contribute to reactivity and cross-reactivity of the reporter system.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

As used herein, a "target transcript" refers to a portion of a nucleotide sequence of a DNA sequence or an mRNA that is naturally formed by a target cell including that formed during the transcription of a target gene and mRNA that is a product of RNA processing of a primary transcription product. The target transcript can also be referred to as a cellular transcript or naturally occurring transcript.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, transduction particles, liposomes, polymers, virus-like particles, and ballistic means. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors can be injected into a tissue site or administered systemically. In vitro introduction into a cell includes methods known in the art, such as transformation, electroporation, transduction, and lipofection. Further approaches are described herein or known in the art.

A "mechanism for the antimicrobial susceptibility phenotype" refers to one or more mechanisms (e.g., one or more genes, mRNAs, and/or proteins) that are involved in imparting resistance or susceptibility of an organism to an antimicrobial agent.

As used herein, the term "molecule" means any compound, including, but not limited to, a small molecule, peptide, protein, sugar, nucleotide, nucleic acid, lipid, etc., and such a compound can be natural or synthetic.

An "oligonucleotide molecule" refers to a molecule that includes nucleic acids that binds a specific target nucleic acid sequence. Oligonucleotide molecules include single stranded molecules, double stranded molecules, antisense molecules, double stranded RNA, PNA, CRISPR RNA, DNAi, etc. Typically an oligonucleotide molecule specifically binds a target nucleic acid sequence (e.g., DNA or RNA). Binding of the oligonucleotide molecule to a specific nucleic acid sequence will typically result in inhibition of the nucleic acid sequence, e.g., via a reduction in expression of the nucleic acid sequence. Binding of the oligonucleotide molecule to a specific nucleic acid sequence can result in blockade or destruction of the nucleic acid sequence.

An "antisense molecule" refers to a molecule that exhibits antisense activity by specifically binding DNA or RNA to inhibit gene expression. Antisense molecules generally include a nucleic acid oligomer having a complementary sequence to its target DNA or RNA. Examples of antisense molecules include antisense oligonucleotides (DNA or RNA), peptide nucleic acids (PNAs), and phosphorodiamidate morpholino (PMO) oligomers.

An "antimicrobial agent" refers to a compound that can kill, inhibit the growth, or otherwise compromise the viability of one or more microorganisms. Antimicrobial agents include antibiotics, antifungals, antiprotozoals, antivirals, and other compounds.

A "detectable indication of viability" refers to an indicator associated with a cell that can be observed and that demonstrates whether the cell is more or less viable or if its viability is affected, e.g., relative to a control cell, where the control cell can be the same cell at a different time point or a separate cell. Examples include one or more signals, one or more reporters, one or more markers, growth or lack thereof, light (e.g., light emitted by a luciferase) or lack thereof, etc.

A virus-based reporter or bacteriophage-based reporter can refer to a virus or bacteriophage, respectively, which has been modified such that a reporter gene has been inserted in its genome.

A "transduction particle" refers to a virus capable of delivering a non-viral nucleic acid molecule into a cell. The virus can be a bacteriophage, adenovirus, etc. A transduction particle reporter can be synonymous with a virus or bacteriophage-based reporter.

A "non-replicative transduction particle" (NRTP) refers to a virus capable of delivering a non-viral nucleic acid molecule into a cell, but does not package its own replicated viral genome into the transduction particle. The virus can be a bacteriophage, adenovirus, etc. NRTPs and methods of making the same are described in detail in PCT/US2014/026536, filed on Mar. 13, 2014, which is incorporated by reference in its entirety for all purposes.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host.

A "vector" is a molecule that includes nucleic acids that can be used as a vehicle to carry genetic material into a cell, where it can be integrated, replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects this nucleic acid; and in some cases, iii) an envelope of lipids that surrounds the protein coat. When referring to a virus that infects bacteria, the terms "virus", "phage" and "bacteriophage" are used interchangeably in the specification.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold or greater. Typically, the affinity or avidity of a specific binding reaction, as quantified by a dissociation constant, is about $10^{-7}$ M or stronger (e.g., about $10^{-8}$ M, $10^{-9}$ M or even stronger).

The term "ameliorating" refers to any therapeutically beneficial result in the treatment of a disease state, e.g., a disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "microorganism" means prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The terms "marker" or "markers" encompass, without limitation, lipids, lipoproteins, proteins, cytokines, chemokines, growth factors, peptides, nucleic acids, genes, and oligonucleotides, together with their related complexes, metabolites, mutations, variants, polymorphisms, modifications, fragments, subunits, degradation products, elements, and other analytes or sample-derived measures. A marker can also include mutated proteins, mutated nucleic acids, variations in copy numbers, and/or transcript variants.

The term "sample" can include a single cell or multiple cells or fragments of cells or an aliquot of body fluid, taken from an environment or subject, by means including venipuncture, excretion, ejaculation, massage, biopsy, needle aspirate, lavage sample, scraping, surgical incision, swabbing, or intervention or other means known in the art.

The term "subject" encompasses a cell, tissue, or organism, human or non-human, whether in vivo, ex vivo, or in vitro, male or female.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine can be replaced in the nucleotide sequences by a nucleotide containing, for example, inosine. Sequences comprising such replacement moieties are embodiments.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term stringent hybridization conditions refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part I, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to produce a detectable signal from a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

NRTPs and Reporter Assays

Non-replicative transduction particles (NRTPs) and methods of producing NRTPs are described in PCT Application No. PCT/US2014/026536, filed on Mar. 13, 2014 and in U.S. patent application Ser. No. 14/550,335, filed on Nov. 21, 2014, the entire disclosures of both are incorporated by reference in their entireties for all purposes. In some embodiments, NRTPs are produced in a bacterial cell packaging system using Disruption/Complementation-based methods. This non-replicative transduction particle packaging system is based on introducing a mutation, silent mutation, insertion, or a deletion into a component of the genome of a virus/bacteriophage that is recognized by the viral/phage packaging machinery as the element from which genomic packaging is initiated during viral/phage production. Examples of such an element include the pac-site sequence of pac-type bacteriophages and the cos-site sequence of cos-type bacteriophages.

Because these packaging initiation sites are often found within coding regions of genes that are essential to virus/bacteriophage production, the mutation, silent mutation, insertion, or a deletion is introduced such that the pac-site is no longer recognized as a site of packaging initiation by the viral/phage packaging machinery. At the same time, in the case of a silent mutation, the mutation does not disrupt the gene in which the site is encoded. By rendering the packaging site sequence non-functional, the mutated virus/bacteriophage is able to undergo a lytic cycle, but is unable to package its genomic DNA into its packaging unit.

An exogenous reporter nucleic acid molecule, such as plasmid DNA, can be introduced into a host bacteria cell that has been lysogenized with a viral/phage genome with a non-functional packaging initiation site sequence. The exogenous reporter nucleic acid molecule can include a native functional packaging initiation site sequence and, in the case where the gene encoding the packaging initiation site sequence is disrupted, the exogenous reporter nucleic acid molecule also includes a corresponding native functional gene. The exogenous reporter nucleic acid molecule can be introduced into the host bacteria cell and replicated in the cell. When the mutated virus/bacteriophage is undergoing a lytic cycle, the expressed viral/phage packaging machinery packages the exogenous reporter nucleic acid molecule with the functional packaging initiation site sequence into the viral packaging unit. The viral/phage genome is not packaged into the packaging unit because its packaging initiation site sequence has been disrupted.

Therefore, the present invention contemplates the use of a bacterial cell packaging system for packaging a reporter nucleic acid molecule into a NRTP for introduction into a cell, which comprises a host bacteria cell, a first nucleic acid construct inside the host bacteria cell, comprising of a bacteriophage genome having a non-functional packaging initiation site sequence, wherein the non-functional packaging initiation site sequence prevents packaging of the bacteriophage genome into the NRTP, and a second nucleic acid construct inside the host bacteria cell and separate from the first nucleic acid construct, comprising of the reporter nucleic acid molecule having a reporter gene and a functional packaging initiation site sequence for facilitating packaging of a replicon of the reporter nucleic acid molecule into the NRTP, wherein the functional second packaging initiation site sequence on the second nucleic acid construct complements the non-functional packaging initiation site sequence in the bacteriophage genome on the first nucleic acid construct.

In some embodiments, constructs (including NRTPs) comprise a reporter nucleic acid molecule including a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (luxA, luxB, luxAB, luc, mc, nluc, etc.). Reporter molecules can include a bacterial luciferase, a eukaryotic luciferase, an enzyme suitable for colorimetric detection (lacZ, HRP), a protein suitable for immunodetection, such as affinity peptides (His-tag, 3X-FLAG), a nucleic acid that function as an aptamer or that exhibits enzymatic activity (ribozyme), or a selectable marker, such as an antibiotic resistance gene (ampC, tet(M), CAT, erm). Other reporter molecules known in the art can be used for producing signals to detect target nucleic acids or cells.

In other aspects, the reporter molecule comprises a nucleic acid molecule. In some aspects, the reporter molecule is an aptamer with specific binding activity or that exhibits enzymatic activity (e.g., aptazyme, DNAzyme, ribozyme).

Disclosed herein are systems for the detection of intracellular enzymes within viable cells that employs caged substrate molecules that can be un-caged by a target intracellular enzyme.

Delivery of cell reporter nucleic acid molecules may be accomplished by various means including electroporation, chemical, biolistic, and glass bead transformation, transduction, transfection, vectors, conjugation, including, but not limited to, delivery via nucleic acid delivery vehicles including bacteriophage, virus, spheroplast, liposomes, virus-like particles, lipid-DNA complexes, lipoplexes, polymer-DNA complexes, polyplexes, etc.

Oligonucleotide Molecules and Antimicrobial Susceptibility Mechanism Determination Disclosed herein are methods for determining the identity of an organism and the mechanisms that impart an antimicrobial resistance or susceptibility to an organism. These methods include suppressing the signal, viability, and/or growth produced from specific strains and species of organisms in cell-reporter systems by suppressing a specific function of an organism that is linked to the organism's viability and/or ability to produce a selectable or detectable marker/signal.

In some embodiments, suppression of the signal, viability, and/or growth produced from specific strains and species of organisms is accomplished by targeting DNA or RNA in non-target organisms. The targeting of nucleic acid molecules in organisms that are not the target of a reporter assay for the purpose of suppressing the signal, viability, and/or growth of these non-target organisms can be accomplished using oligonucleotide regulation in which strain and species-specific molecules are targeted by design. In this sense, "targeting" is accomplished using molecules that can hybridize to the target nucleic acid through a complementary sequence.

The exemplary targets disclosed herein are non-limiting examples that are described in the application and can be extended beyond these examples to include any sequence target that an oligonucleotide molecule can bind to including genes, transcripts, non-coding RNAs, etc.

Oligonucleotide molecules can be employed to target a single sequence or a plurality of sequences by incorporating multiple oligonucleotide molecules targeting different sequences in a single assay. As such, an assay can target a single gene, different genes, or different variants of a single gene.

Oligonucleotide molecules can be of any type including, but not limited to nucleic acid oligonucleotides, oligonucleotide analogues, oligonucleotide mimics, DNA minor groove binding polyamides, PNA, LNA, phophorothioate, 2'-methoxy-, 2'-methoxyetoxy-, morpholino, phophoramidate, etc.

Delivery of oligonucleotide molecules may be accomplished via exogenous addition of the molecules or their in situ expression. Exogenous delivery be facilitated by conjugation of the molecule to a peptide or by other means including, but not limited to, delivery via liposomes, etc. In situ expression mediated by nucleic acid designed to express oligonucleotides within a target organism may be accomplished via any means of delivering nucleic acid into the target organism including electroporation, chemical, biolistic, and glass bead transformation, transduction, transfection, conjugation, including, but not limited to, delivery via nucleic acid delivery vehicles including bacteriophage, virus, spheroplast, liposomes, virus-like particles, lipid-DNA complexes, lipoplexes, polymer-DNA complexes, polyplexes, etc.

Delivery of cell reporter nucleic acid molecules may be accomplished by various means including electroporation, chemical, biolistic, and glass bead transformation, transduction, transfection, conjugation, including, but not limited to, delivery via nucleic acid delivery vehicles including bacteriophage, virus, spheroplast, liposomes, virus-like particles, lipid-DNA complexes, lipoplexes, polymer-DNA complexes, polyplexes etc.

Antisense RNA regulation occurs in nature via a process in which antisense RNA binds to another RNA molecule (1). Antisense oligonucleotides, Peptide Nucleic Acid (PNA) (2), and Phosphorodiamidate Morpholino (PMO) oligomers have been designed to bind to intracellular nucleic acid targets. For example, PNAs have been used to regulate gene expression in cells in a manner analogous to natural antisense RNA regulation (3-5). Antisense molecules can be of any type including, but not limited to oligonucleotides, oligonucleotide analogues, oligonucleotide mimics, DNA minor groove binding polyamides, PNA, LNA, phophorothioate, 2'-methoxy-, 2'-methoxyetoxy-, morpholino, phophoramidate etc. Delivery of antisense molecules may be facilitated by conjugation of the molecule to a peptide or by other means including, but not limited to, delivery via liposomes, conjugation to peptides, delivery via DNA delivery vehicles designed to transcribe antisense molecules, etc. Peptide-PNAs are PNA's that are conjugated to a peptide. Peptide-PNAs have been used to target RNA molecules in bacteria where the peptide is designed to facilitate uptake of the molecule into the bacteria (6).

Antisense molecules can be designed to target specific strains and species of bacteria (7). By analyzing the genome of the bacteria of interest, a set of antisense molecule targets can be identified that target essential genes in a manner that the targeting is specific to one species of bacteria and not another. In this manner, the antisense molecule can be tuned to suppress individual species of bacteria.

Oligonucleotides and oligomers can be delivered into cells via a variety of mechanisms that facilitate uptake into cells including liposomes and conjugation to peptides. Peptide-PNAs are PNAs that are conjugated to a peptide. Peptide-PNAs have been used to target RNA molecules in bacteria, such that the peptide is designed to facilitate uptake of the molecule into the bacteria (Good, L. and P. E. Nielsen, WO 2002/0279467).

Antisense molecules can be designed to target specific strains and species of bacteria (Mondhe, M., et al., *Species-Selective Killing of Bacteria by Antimicrobial Peptide-PNAs*. PLoS ONE, 2014. 9(2): p. e89082). By analyzing the genome of the bacteria of interest, a set of antisense molecule targets can be identified that target essential genes in a manner that the targeting is specific to one species of bacteria and not another. In this manner, the antisense molecule can be tuned to suppress specific individual species of bacteria.

In an embodiment, a system is designed to knock down the expression of a target phenotype such as the expression of an antimicrobial resistance mechanism. Oligonucleotide molecules can be designed to target the transcripts of resistance genes such that a microorganism that is normally resistant to an antimicrobial compound becomes sensitive to the compound upon exposure to the targeting oligonucleotide.

In addition to employing exogenous oligonucleotides, targeting oligonucleotides can be produced in vivo from DNA delivered into a target organism. In this embodiment, the DNA is designed to transcribe antisense RNA molecules designed to target transcripts of interest.

In another embodiment, RNA interference (RNAi) can be employed; a process in which double-stranded RNA fragments (dsRNA, also called small interfering RNAs (siRNAs)) trigger catalytically mediated gene silencing, most typically by targeting the RNA-induced silencing complex (RISC) to bind to and degrade the mRNA. Annealing of a strand of the dsRNA molecule to mRNA or DNA can result in fast degradation of duplex RNA, hybrid RNA/DNA duplex, or duplex RNA resembling precursor tRNA by ribonucleases in the cell, or by cleavage of the target RNA by the antisense compound itself.

The RNAi pathway is found in many eukaryotes and is initiated by the enzyme Dicer, which cleaves long double-stranded RNA (dsRNA) molecules into short double stranded fragments of ~20 nucleotides that are called siRNAs. Each siRNA is unwound into two single-stranded RNAs (ssRNA), namely the passenger strand and the guide strand. The passenger strand is degraded, and the guide strand is incorporated into the RNA-induced silencing complex (RISC). In post-transcriptional gene silencing, the guide strand base pairs with a complementary sequence in a messenger RNA molecule, and cleavage is induced by a protein called Argonaute, the catalytic component of the RISC complex.

Interactions between an oligonucleotide and a target transcript can rely on base pairings between loops present in both transcripts (e.g., "kissing complexes"), or between a loop and a single-stranded (ss) region. In some cases, the kissing complex formation suffices for mediating the desired effect of the interaction, and in other cases, propagation of the primary contacts will lead to an interaction resulting in the desired effect.

Another embodiment employing in vivo production of targeting oligonucleotides is based on the clustered, regularly interspaced, short palindromic repeats (CRISPR)/CRISPR-associated (Cas) system that is found in bacteria as a defense against foreign DNA (8). The CRISPR/Cas system can be designed to target a DNA sequence of interest by incorporating target sequences that are transcribed and processed into CRISPR RNAs (crRNA). The system also expresses a trans-activating small RNA (tracrRNA) and a complex formed by Cas9, tracrRNA, and crRNAs enable the Cas9 endonuclease to form double-stranded breaks in target DNA sequences targeted by the crRNA. In this embodiment, crRNA oligonucleotides can be designed in the sense or antisense direction and instead of targeting transcripts, this system targets DNA and thus is designed to target organism-specific DNA sequences or antibiotic resistance genes encoded in the chromosome or episomally.

Similar techniques as described above have been employed in the art for the purpose of developing therapeutic agents against microorganism infections (9-10). As described further herein, these techniques are used for the purpose of enabling bacterial detection systems and for determining specific mechanisms linked to an antimicrobial resistance or susceptibility phenotype(s).

By designing an oligonucleotide molecule to target the specific DNA or RNA sequence of a resistance gene, the specific mechanism linked to a phenotype can be determined. For example, AST is performed on a microorganism, if the microorganism is determined to be resistant to an antimicrobial in question and susceptible to the same antimicrobial when in the presence of the oligonucleotide molecule, then this result indicates that the specific antimicrobial gene for which the oligonucleotide molecule is designed to target is linked to the antimicrobial resistance phenotype.

EXAMPLES

Example 1: Elimination of Signal from *E. coli* in Enterobacteriaceae Reporter In this example, an Enterobacteriaceae reporter system was used in conjunction with a peptide-PNA targeting *E. coli*. Without the use of peptide-PNA, the Enterobacteriaceae reporter system produces a detectable signal from Enterobacteriaceae, including both *K. pneumoniae* and *E. coli*. When the peptide-PNA was added, the Enterobacteriaceae reporter system produced signal from Enterobacteriaceae, excluding *E. coli*. The system may be employed with and without the oligonucleotide and the presence of the target organism can be determined by the observation that a signal is present without the peptide-PNA and is not present with the peptide-PNA. Alternatively, in a sample that may contain both *E. coli* and *K. pneumoniae*, the running of the assay in the presence of the oligonucleotide allows for the determination if *K. pneumoniae* is present in the sample. In this example, a sample that only contains *K. pneumoniae* will produce signal whether or not *E. coli* is also present in the sample while a sample that only contains *E. coli* will not produce a signal. In this manner, peptide-PNA can be used to achieve species-specific bacterial detection.

A peptide-PNA was designed to target an essential gene of *E. coli* following (7). Briefly, the genomes of *E. coli* and *K. pneumoniae* were analyzed to identify essential gene homologues present in the species of interest. From this analysis a list of the translation initiation region (TIR) for each gene was compiled—i.e. twenty base-pairs (−10 to +10 bases relative to the start codon) of the TIRs in the genomes. The 20 base-pair TIRs from gene homologues were aligned and the number of base-pair mismatches between species was determined. Antisense sequences of 9-12 bp targeting a region within the TIR were used to design the PNAs. The predicted thermal stability of PNA/DNA duplexes was determined and a genomic analysis of the possible binding sites of the PNAs within the target species was conducted using a cut-off of greater than 2 base-pair mismatches.

From this analysis potential binding sites of each PNA can be identified for a gene homologue, for example, in which one PNA binds to the homologue of one species but not the other and vice versa. The *E. coli*-specific PNA targeting the murA gene was identified to be the sequence set forth in SEQ ID NO 1. A peptide-PNA targeting this sequence is thus expected to bind to *E. coli* murA but not *K. pneumoniae* murA.

The PNA was conjugated to the peptide KFFKFFKFFK (SEQ ID NO 10) following (11) since this peptide has been demonstrated to facilitate penetration of PNA into bacterial cells. Thus, the sequence of the *E. coli* murA-targeting peptide-PNA is as follows: KFFKFFKFFK-eg-ccatttagtt (murA PNA), where eg is an ethylene glycol linker derived from [2-[2-(Fmoc-amino)ethoxy]ethoxy]acetic acid.

Effect of murA PNA on the Growth of *E. coli* and *K. pneumoniae:*

The effect of the murA PNA on the growth of *E. coli* and *K. pneumoniae* was examined. When *E. coli* and *K. pneumoniae* were cultured in the presence of murA PNA, the growth of *E. coli* was compromised while the growth of *K. pneumoniae* was not.

Isolates of *E. coli* and *K. pneumoniae* were grown overnight in LB at 37° C. and sub-cultured the next day at a 1:100 dilution into fresh LB and grown to an optical density at 600 nm (OD600) of 0.2. Inoculums of each strain of approximately $10^4$ CFU of each species of bacteria were added to separate wells of a microplate each containing 50 μL of LB or LB with murA PNA at a final concentration of 4.5 μM. OD600 readings were measured over a period of 8 hours to assess growth of PNA-treated and PNA-untreated cells.

Figure 2:
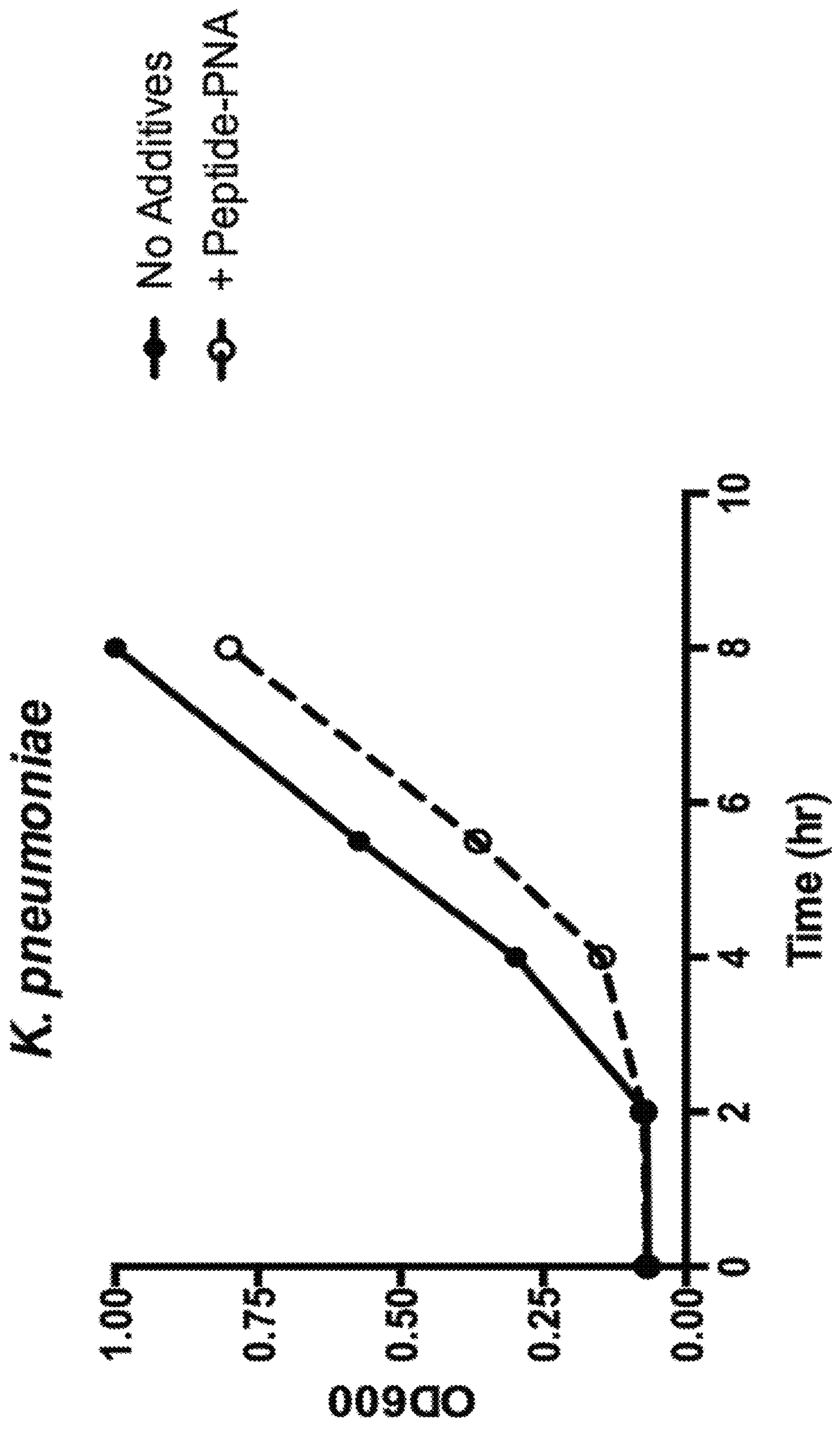
FIG. 2 shows the effect of *E. coli*-specific peptide-PNA on the growth of *K. pneumoniae.*

FIG. 1 depicts the results of the growth experiment for *E. coli*. In the presence of PNA, the growth of *E. coli* was compromised. FIG. 2 depicts the results of the growth experiment for *K. pneumoniae*. In the presence of PNA, the growth of *K. pneumoniae* was not compromised. The results indicate that the murA PNA specifically inhibits the growth of *E. coli* and does not inhibit the growth of *K. pneumoniae*.

Effect of murA PNA on the Luminescence of an Enterobacteriaceae Reporter when Testing *E. coli* and *K. pneumoniae:*

Isolates of *E. coli* and *K. pneumoniae* were grown overnight in LB at 37° C. and sub-cultured the next day at a 1:100 dilution into fresh LB and grown to an OD600 of 0.2. Inoculums of each strain of approximately $10^4$ CFU of each species of bacteria were added to separate wells of a microplate each containing 50 μL of LB or LB with murA PNA at a final concentration of 4.5 μM. All wells subsequently received 100 uL of an Enterobacteriaceae luminescent-reporter non-replicative transduction particle as described in PCT/US2014/026536, Example 1 and the samples were incubated at 30° C. for 2 hours. After the incubation period, the plates were assayed for luminescence using a Molecular Devices SpectraMax L microplate luminometer in which a solution of tridecanal was injected into each well as luminescence readings were taken.

Figure 3:
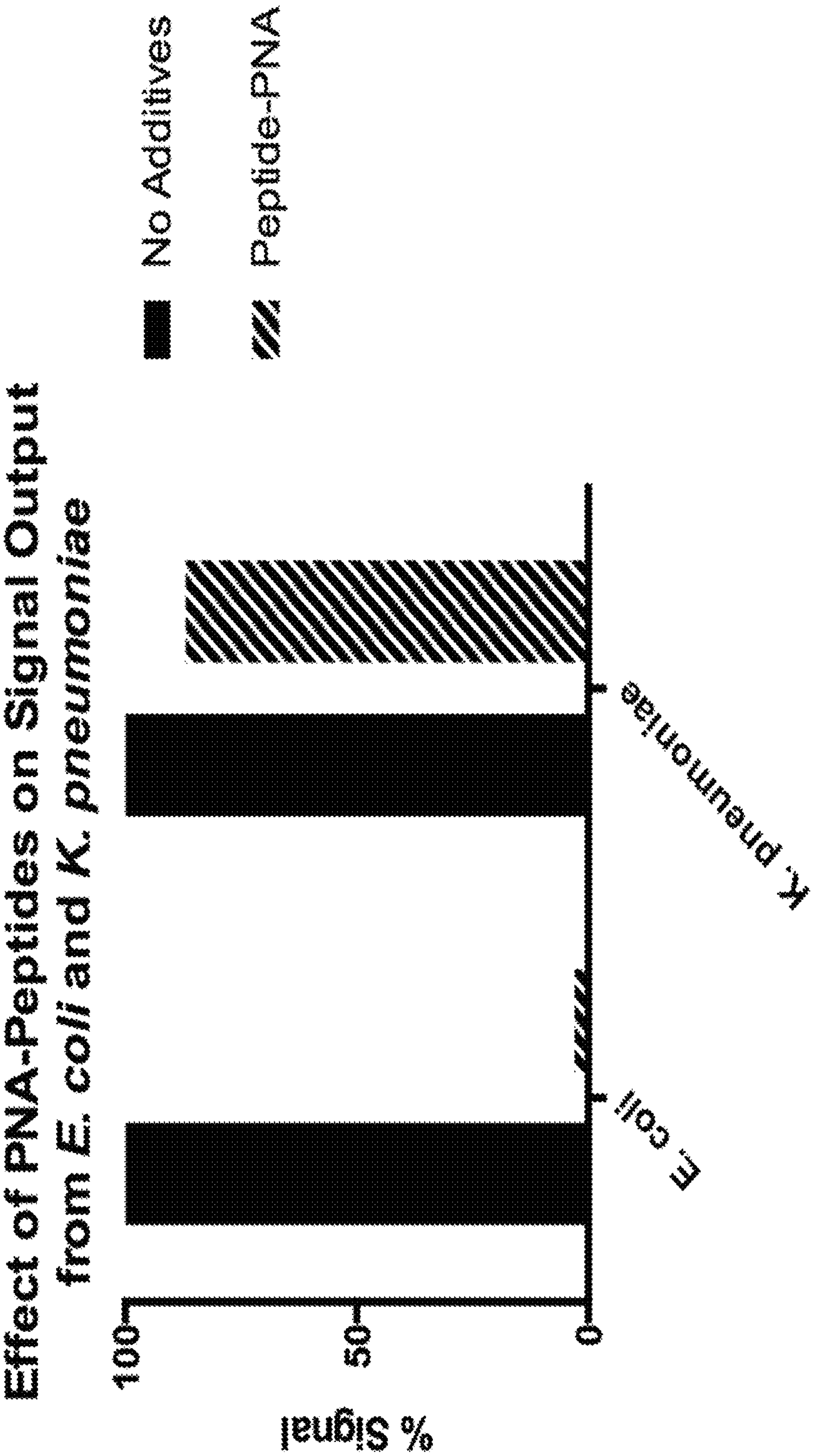
FIG. 3 shows the effect of *E. coli*-specific peptide-PNA on the luminescence signal from *E. coli* and *K. pneumoniae* using an Enterobacteriaceae luminescence reporter.

FIG. 3 depicts the results of the luminescence experiment for *E. coli* and *K. pneumoniae*. In the presence of PNA, the luminescence signal produced by *E. coli* was compromised while the luminescence signal produced by *K. pneumoniae* was not. The results indicate that the murA PNA specifically inhibits signal production from *E. coli* and does not inhibit signal production from *K. pneumoniae* demonstrating the ability of distinguishing *E. coli* from *K. pneumoniae* using an Enterobacteriaceae reporter system and an *E. coli*-specific Peptide-PNA.

Example 2: Determination of Specific Carbapenemase Linked to a CRE Phenotype Via AST Antimicrobial Disk Diffusion Testing Using Peptide-PNA In this example, AST antimicrobial disk diffusion testing is performed with the addition of peptide-PNA on a CRE strain in order to determine the specific mechanism linked to the CRE phenotype. Without the use of peptide-PNA, the CRE exhibits a carbapenem-resistant result. When peptide- PNA designed to target a specific carbapenemase gene is added and the AST result changes to a carbapenem-susceptible (CSE) phenotype, this indicates that the carbapenemase gene targeted by the peptide-PNA is the mechanism linked to the CRE phenotype. In this manner, peptide-PNA can be used to determine the specific mechanism linked to the antimicrobial resistance phenotype of the bacteria.

A peptide-PNA is designed to target $bla_{KPC\text{-}3}$ and $bla_{NDM\text{-}1}$ transcripts of *E. coli*. Briefly, the gene sequences of the target genes in *E. coli* 1289012 and *E. coli* 1289014, two clinical isolates of *E. coli* that express a $bla_{KPC\text{-}3}$ and $bla_{NDM\text{-}1}$ genes, respectively, are analyzed to identify the sequence of the TIR for each gene (Table 1, SEQ ID NOs 11 & 12). Antisense sequences of 9-12 bp targeting a region within the TIR are used to design the potential PNAs. From this analysis potential binding sites of for PNA can be identified for targeting the $bla_{KPC\text{-}3}$ (SEQ ID NO 2) and $bla_{NDM\text{-}1}$ (SEQ ID NO 3) genes.

The PNA is conjugated to the peptide KFFKFFKFFK following (11) since this peptide has been demonstrated to facilitate penetration of PNA into bacterial cells.

AST Testing Disk Diffusion Testing:

Disk diffusion testing is conducted following CLSI-M02 (12) and interpreted following M100-S22 (13). Briefly, for testing each bacterium for susceptibility to meropenem, a Mueller-Hinton agar (MHA) plates are inoculated using a sterile cotton swab dipped into a suspension of a culture of bacteria at a 0.5 McFarland standard such that the entire surface of the MHA is covered. A 10 μg meropenem disk is applied to the surface of the inoculated plate and the plate is incubated at 35° C. in ambient air for 16 to 18 hours. The strain of bacteria is determined to be susceptible to meropenem if the diameter of the zone of inhibition around the meropenem disk is ≥23 mm and resistant to meropenem if the zone diameter is ≤19 mm.

*E. coli* 1289012, 1289014, a control *E. coli* 1289018 that is CSE and does not express a carbapenemase, and *E. coli* 1289011 a control strain that is CRE and that expresses an VIM carbapenemase are tested for meropenem resistance via disk diffusion. The second row of FIG. 4 depicts the typical meropenem disk diffusion results for the *E. coli* strains where 1289011, 1289012, and 1289014 are CRE and 1289018 is CSE.

To determine the specific mechanism linked to the meropenem-resistant phenotype, disk diffusion testing is conducted with 10 μg meropenem disks including $bla_{KPC\text{-}3}$- and $bla_{NDM\text{-}1}$-peptide-PNA. If the peptide-PNA inhibits the specific carbapenemase linked to the meropenem resistance in the *E. coli* strain, then the zone diameter observed will be decreased when compared to the zone diameter of the strain when exposed to a disk containing only meropenem.

Figure 4:
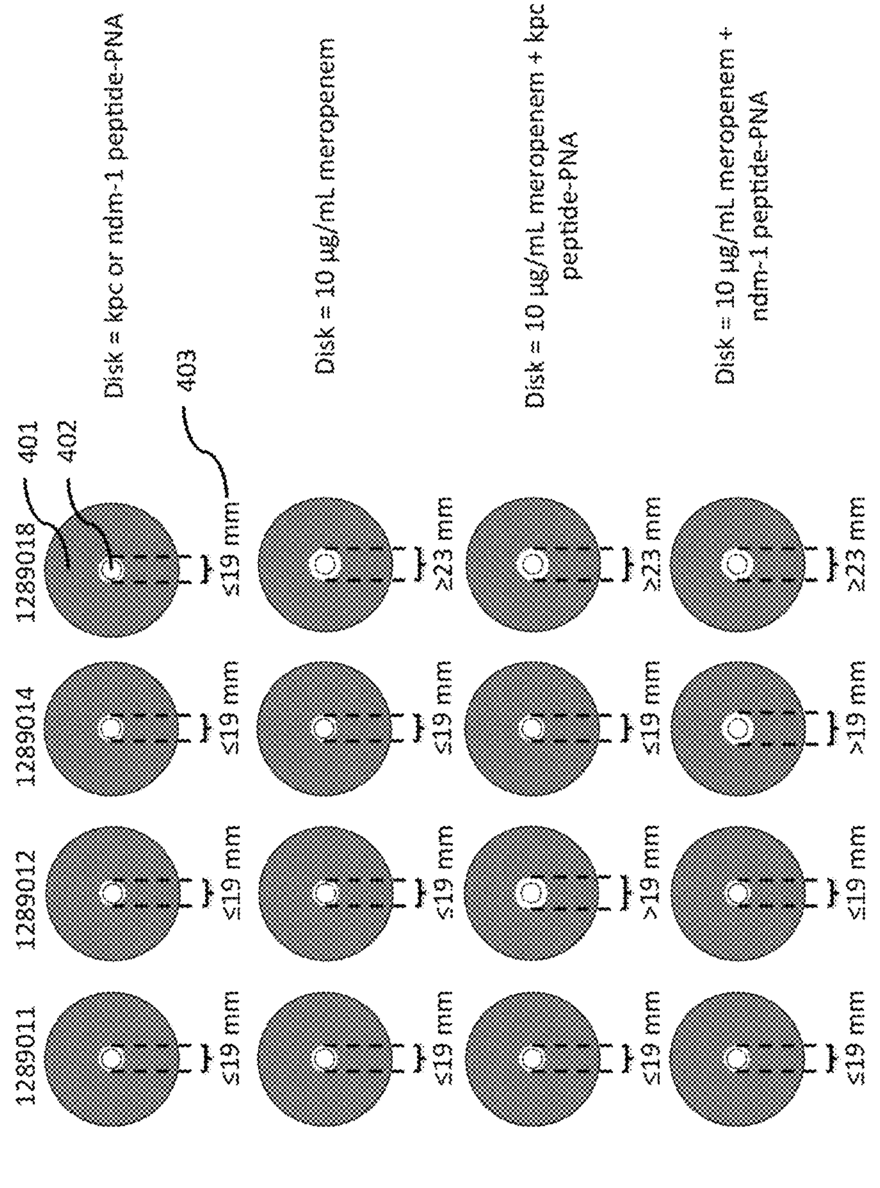
FIG. 4 depicts an example of typical meropenem/peptide-PNA disk diffusion results for *E. coli* 1289011, 1289012, 1289014, and 1289018.

FIG. 4 depicts the typical meropenem/peptide-PNA disk diffusion results for *E. coli* 1289011, 1289012, 1289014, and 1289018. In the figure, 401 depicts a top-view of a petri dish that contains MHA and a lawn of bacteria grown on the surface of the agar, 402 depicts a disk that has been placed on the surface of 401, and 403 indicates the zone diameter that results on the lawn of bacteria due to the contents of the disk 402.

The top row in the figure demonstrates that the peptide-PNA alone does not have an inhibitory effect on the *E. coli* strains. Row 3 demonstrates that 1289011 is CRE since the zone diameter is ≥23 mm and the mechanism linked to the CRE phenotype is not $bla_{KPC\text{-}3}$ since in the presence of $bla_{KPC\text{-}3}$ peptide-PNA, the zone diameter is not reduced when compared to that of meropenem alone, 1289012 is CRE where $bla_{KPC\text{-}3}$ is the mechanism linked to the CRE phenotype since the zone diameter is reduced, and 1289014 is CRE and the mechanism linked to the CRE phenotype is not $bla_{KPC\text{-}3}$ since the zone diameter is not reduced. Row 4 demonstrates that 1289011 is CRE since the zone diameter is ≥23 mm and the mechanism linked to the CRE phenotype is not $bla_{NDM\text{-}1}$ since in the presence of $bla_{NDM\text{-}1}$ peptide-PNA, the zone diameter is not reduced when compared to that of meropenem alone, 1289012 is CRE and the mechanism linked to the CRE phenotype is not $bla_{NDM\text{-}1}$ since the zone diameter is not reduced, and 1289014 is CRE where $bla_{NDM\text{-}1}$ is the mechanism linked to the CRE phenotype since the zone diameter is reduced.

From these results, it can be determined that the underlying mechanism linked to the carbapenem resistance each strain of *E. coli* is $bla_{KPC\text{-}3}$ for 1289012, $bla_{NDM\text{-}1}$ for 1289014, and neither $bla_{KPC\text{-}3}$ nor $bla_{NDM\text{-}1}$ in 1289011.

Example 3: Determination of Specific Carbapenemase Linked to a CRE Phenotype Via AST Cell-Reporter Testing Using Peptide-PNA In this example, the AST technique described in Example 2 is extended to AST testing based on cell-reporter assays. An Enterobacteriaceae cell reporter as described in PCT/US2014/026536, Example 1 is employed and the assay is run as follows. Briefly, cultures of *E. coli* 1289011, 1289012, 1289014, and 1289018 are prepared and used to inoculate wells of a microwell plate containing 50 μL of LB with 50 μL of inoculum such that each well receives $10^4$ CFU of each strain of bacteria. A set of wells contain no additional additives, another set of wells contain 5 μg/mL of meropenem, another set of wells contain 5 μg/mL of meropenem and $bla_{KPC\text{-}3}$-peptide-PNA, another set of wells contain 5 μg/mL of meropenem and $bla_{NDM\text{-}1}$-peptide-PNA, and another two set of wells contain only $bla_{KPC\text{-}3}$ or $bla_{NDM\text{-}1}$ peptide-PNA, respectively. All wells also receive 100 μL of the Enterobacteriaceae reporter. The samples are then incubated at 30° C. for 2 hours and then the samples are assayed for luminescence as described in Example 1.

FIG. 5 depicts the results of the cell-reporter AST assay where + indicates that the reporter assay produced a positive result and − indicates that the reporter assay produced a negative result.

Column 1 indicates that the Enterobacteriaceae reporter gives a positive signal for all of the *E. coli* strains. Column 5 demonstrates that peptide-PNA does not inhibit a positive result in any of the *E. coli* strains. Column 2 indicates that all of the *E. coli* strains are CRE except for 1289018 since all of the *E. coli* strains except for 1289018 continue to give a positive signal in the presence of meropenem. Column 3 demonstrates that 1289011 and 1289014 are CRE and the mechanism linked to the CRE phenotype is not $bla_{KPC\text{-}3}$ since in the presence of meropenem and $bla_{KPC\text{-}3}$ peptide-PNA it continues to produce a positive signal, and 1289012 is CRE where $bla_{KPC\text{-}3}$ is the mechanism linked to the CRE phenotype since in the presence of meropenem and $bla_{KPC\text{-}3}$ peptide-PNA it no longer produces a positive signal. Column 4 demonstrates that 1289011 and 1289012 are CRE and the mechanism linked to the CRE phenotype is not $bla_{NDM\text{-}1}$ since in the presence of meropenem and $bla_{NDM\text{-}1}$ peptide-PNA it continues to produce a positive signal, and 1289014 is CRE where $bla_{NDM\text{-}1}$ is the mechanism linked to the CRE phenotype since in the presence of meropenem and $bla_{NDM\text{-}1}$ peptide-PNA it no longer produces a positive signal.

From these results, it can be determined that the mechanism linked to the carbapenem resistance phenotype in each strain of *E. coli* is $bla_{KPC-3}$ for 1289012, $bla_{NDM-1}$ for 1289014, and neither $bla_{KPC-3}$ nor $bla_{NDM-1}$ in 1289011.

Example 4: Determination of Specific β-Lactamase Linked to a Non-Susceptible Phenotype Via AST Cell-Reporter Testing Using CRISPR/Cas9

In this example, the AST technique described in Example 3 is modified to determine the specific β-lactamase linked to a CRE phenotype using a CRISPR/Cas9 system designed to target plasmid-encoded β-lactamase genes.

Enterobacteriaceae cell reporters as described in PCT/US2014/026536, Example 1 are designed with reporter plasmids that also carry single-guide[14] CRISPR/Cas9 systems with CRISPR loci that carry sequences targeting $bla_{NDM-1}$ and $bla_{SHV-18}$ genes (Table 1, SEQ ID NOs 11 & 13) a carbapenem resistance and extended β-lactam resistance gene, respectively. The reporter plasmid pGWP10001 is modified to include the cas9 gene, tracrRNA under the control of the $P_{L(tetO-1)}$ promoter, and a CRISPR cloning site, and CRISPR loci are designed to target the $bla_{NDM-1}$ (SEQ ID NO 4) and $bla_{SHV-18}$ (SEQ ID NO 5) genes and each are cloned into pGWP10001/CRISPR/Cas9 vectors to generate reporter plasmids that simultaneously target the $bla_{NDM-1}$ and $bla_{SHV-18}$ genes.

The vectors are used to generate non-replicative transduction particles carrying each plasmid and these are employed in a reporter system for determining the mechanism responsible to β-lactam non-susceptibility. Briefly, cultures of *E. coli* 1289018 ($bla_{NDM-1}$, $bla_{SHV-18}$-negative), 1289023 ($bla_{NDM-1}$-positive), 1289027 ($bla_{SHV}$-positive), and 1289011 ($bla_{VIM}$-positive) are prepared and used to inoculate wells of a microwell plate containing 50 μL of LB with 50 μL of inoculum such that each well receives $10^4$ CFU of each strain of bacteria. To these wells 100 μL of the following is added: a set of wells contain 5 μg/mL of meropenem and $bla_{NDM-1}$-targetting NRTP, another set of wells contain 5 μg/mL of meropenem and $bla_{SHV-18}$-NRTP, another set of wells contain 5 μg/mL of ceftazidime and $bla_{NDM-1}$-targetting NRTP, and another set of wells contain 5 μg/mL of ceftazidime and $bla_{SHV-18}$-NRTP. The samples are then incubated at 30° C. for 2 hours and then the samples are assayed for luminescence as described in Example 1.

FIG. 6 depicts the results of the cell-reporter AST assay where + indicates that the reporter assay produced a positive result and – indicates that the reporter assay produced a negative result.

Row 1 indicates that strain 1289018 is inhibited by meropenem and ceftazidime regardless of which NRTP is included in the assay and thus likely carries neither $bla_{NDM-1}$ nor $bla_{SHV-18}$. Row 2 indicates that strain 1289023 is only inhibited by the β-lactams when in the presence of the $bla_{NDM-1}$-targetting NRTP and thus likely carries the $bla_{NDM-1}$ gene. Row 3 indicates that strain 1289027 is inhibited in the presence of meropenem and is inhibited in the presence of ceftazidime only when also in the presence of the $bla_{SHV-18}$-targetting NRTP and thus likely carries a $bla_{SHV-18}$ gene. Row 4 indicates that strain 1289011 is not inhibited by any of the β-lactams regardless of the NRTP included in the assay and thus likely carries a carbapenem-resistance mechanism that is not mediated by only $bla_{NDM-1}$.

From these results, it can be determined that the mechanism linked to the β-lactam resistance phenotype in strain 1289023 is $bla_{NDM-1}$ and in strain 1289027 is $bla_{SHV-18}$.

Example 5: Vancomycin-Resistant *Enterococcus* Assay

In another embodiment, an assay for the detection of vancomycin-resistant *Enterococcus* (VRE) may be developed.

VRE consists of *Enterococcus* spp. that have acquired vancomycin-resistance via resistance genes including the vanA and vanB genes. *Enterococcus* spp. that carry other vancomycin-resistance genes and express other vancomycin resistance phenotypes including the VanC phenotype encoded by genes including vanC-1,vanC-2, and vanC-3, however, such organisms are not considered VRE.

In this example an *Enterococcus* cell reporter is employed in combination with vancomycin and antisense molecules targeting vanC-2 gene expression. The assay allows for the detection of VRE and discrimination from vancomycin-sensitive *Enterococcus* (VSE) and *Enterococcus* expressing the vanC-2 gene and not the vanA or vanB genes. The *Enterococcus* reporter is designed to cause *Enterococcus* spp. to produce a detectable signal. A Peptide-PNA is designed to target vanC-2 transcripts. The gene sequences of the target genes in *E. casseliflavus* 1279015, a clinical isolate that express the vanC-2 gene (Table 1, SEQ ID NO 14), is analyzed to identify the sequence of the TIR for the gene. Antisense sequences of 9-12 bp targeting a region within the TIR are used to design the potential PNAs. From this analysis potential binding sites of for PNA can be identified for targeting the vanC-2 gene (SEQ ID NO 6).

Briefly, cultures of VSE *E. faecalis* 1259012, vanA-positive VRE *E. faecalis* 1259016, VSE *E. faecium* 1269011, vanB-positive VRE *E. faecium* 1269014, and vanC-2-positive vancomycin non-susceptible *E. casseliflavus* 1279015 are prepared and used to inoculate wells of a microwell plate containing 50 μL of LB with 50 μL of inoculum such that each well receives $10^4$ CFU of each strain of bacteria. A set of wells contains no additional additives, another set of wells contains 5 μg/mL of vancomycin, and another set of wells contains 5 μg/mL of vancomycin and vanC-2-peptide-PNA. All wells also receive 100 μL of the *Enterococcus* reporter. The samples are then incubated at 37° C. for 2 hours and then the samples are assayed for luminescence as described in Example 1.

FIG. 7 depicts the results of the cell-reporter assay where + indicates that the reporter assay produced a positive result and – indicates that the reporter assay produced a negative result.

Column 1 indicates that the *Enterococcus* reporter gives a positive signal for all of the *Enterococcus* spp. Column 4 demonstrates that peptide-PNA does not inhibit a positive result in any of the strains. Column 2 indicates that all of the strains expressing a van gene continue to give a positive signal while strains not carrying a van gene do not. Column 3 indicates that only strains expressing a vanA or vanB gene continue to give a positive signal.

These results thus demonstrate that such an assay combining an *Enterococcus* reporter in combination with vancomycin and antisense molecules targeting vanC-2 gene expression can be used to detect VRE.

Example 5: *Candida* Reporter Assay

In another embodiment, a mycology assay for the identification of *Candida* may be developed.

A yeast reporter system designed to cause yeast cells to produce a detectable or selectable marker is applied in combination with antisense molecules that target species-specific sequences. When the system is applied to a sample that contains the target species, the antisense molecule causes the suppression of the signal, viability, and/or growth of the target cell.

The reporter plasmid is based on *E. coli*/yeast vector pLG5 that includes fused *V. harveyi* bacterial luciferase under the control of the GAL1 promoter (15, 16). The species-specific antisense molecules are designed to target sequences within internal transcribed spacer (ITS) regions in yeast. ITS consist of segments of non-functional RNA located between ribosomal RNAs (rRNA) sequences on a transcript from which the ITS are excised during rRNA maturation. The internal transcribed spacer region 2 (ITS2) in *Candida* spp. exhibits sequence specificity that may be used to identify different species of *Candida* (17) and disruption of rRNA maturation by antisense molecules exhibits fungicidal effects (18). FIG. 8 includes a list of ITS2 sequences used for producing 2'-OMe modified antisense oligonucleotides (AON) targeting each species.

Antisense sequences for targeting each species are designed by conducting a sequence alignment between the ITS2 sequences for each species. Sequences of 9-12 bp are chosen that are unique to each species based on the alignment data and these sequence candidates are analyzed for homology across genomic data from a library of potentially cross-reactive organisms. From this analysis sequence candidates can be chosen that are unique to each target species.

Based on this analysis, AON sequences were designed for *Candida albicans, Candida tropicalis*, and *Candida parapsilosis* (SEQ ID NO 7, 8, and 9, respectively).

Briefly, *Candida albicans* 5120012, *Candida tropicalis* 5160014, and *Candida parapsilosis* 5150013 are transformed with the reporter plasmid and AON via intact cell transformation (16). The samples are incubated for a period of 24 hours and assayed for luminescence using as described in Example 1 (19).

FIG. 9 depicts the assay setup for the combination of AON used for *Candida* spp. identification. The results of the cell-reporter assay are shown where + indicates that the reporter assay produced a positive result and – indicates that the reporter assay produced a negative result.

Column 1 indicates that the reporter gives a positive signal for all of the organisms tested in the assay. Columns 2-5 indicate that when AON targeting specific species are included in the assay, samples containing those species then produce a negative result in the assay while samples containing species for which an AON that targets that species is not present in the assay result in a positive result.

These results thus demonstrate that such an assay combining a yeast reporter in combination with antisense oligonucleotide molecules targeting species-specific ITS2-derived sequences can be used to detect specific species of *Candida*.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference, in their entirety, for all purposes.

TABLE 1

| Target Resistance Gene Sequences | | |
|---|---|---|
| $bla_{KPC-3}$ | AGCTGTAGCGGCCTGATTACATCCGGCCGCTACACCTAGCTCCACCTTC<br>AAACAAGGAATATCGTTGATGTCACTGTATCGCCGTCTAGTTCTGCTGT<br>CTTGTCTCTCATGGCCGCTGGCTGGCTTTTCTGCCACCGCGCTGACCAAC<br>CTCGTCGCGGAACCATTCGCTAAACTCGAACAGGACTTTGGCGGCTCCA<br>TCGGTGTGTACGCGATGGATACCGGCTCAGGCGCAACTGTAAGTTACCG<br>CGCTGAGGAGCGCTTCCCACTGTGCAGCTCATTCAAGGGCTTTCTTGCT<br>GCCGCTGTGCTGGCTCGCAGCCAGCAGCAGGCCGGCTTGCTGGACACA<br>CCCATCCGTTACGGCAAAAATGCGCTGGTTCCGTGGTCACCCATCTCGG<br>AAAAATATCTGACAACAGGCATGACGGTGGCGGAGCTGTCCGCGGCCG<br>CCGTGCAATACAGTGATAACGCCGCCGCCAATTTGTTGCTGAAGGAGTT<br>GGGCGGCCCGGCCGGGCTGACGGCCTTCATGCGCTCTATCGGCGATACC<br>ACGTTCCGTCTGGACCGCTGGGAGCTGGAGCTGAACTCCGCCATCCCAG<br>GCGATGCGCGCGATACCTCATCGCCGCGCGCCGTGACGGAAAGCTTAC<br>AAAAACTGACACTGGGCTCTGCACTGGCTGCGCCGCAGCGGCAGCAGT<br>TTGTTGATTGGCTAAAGGGAAACACGACCGGCAACCACCGCATCCGCG<br>CGGCGGTGCCGGCAGACTGGGCAGTCGGAGACAAAACCGGAACCTGCG<br>GAGTGTATGGCACGGCAAATGACTATGCCGTCGTCTGGCCCACTGGGCG<br>CGCACCTATTGTGTTGGCCGTCTACACCCGGGCGCCTAACAAGGATGAC<br>AAGTACAGCGAGGCCGTCATCGCCGCTGCGGCTAGACTCGCGCTCGAG<br>GGATTGGGCGTCAACGGGCAGTAAGGCTCTGAAAATCATCTATTGGCCC<br>ACCACCGCCGCCCTTGCGGGCGGCATGGATTACCAACCACTGTCAC | SEQ ID NO 11 |
| $bla_{NDM-1}$ | AAAGCCCAGCTTCGCATAAAACGCCTCTGTCACATCGAAATCGCGCGAT<br>GGCAGATTGGGGGTGACGTGGTCAGCCATGGCTCAGCGCAGCTTGTCG<br>GCCATGCGGGCCGTATGAGTGATTGCGGCGCGGCTATCGGGGGCGGAA<br>TGGCTCATCACGATCATGCTGGCCTTGGGGAACGCCGCACCAAACGCGC<br>GCGCTGACGCGGCGTAGTGCTCAGTGTCGGCATCACCGAGATTGCCGA<br>GCGACTTGGCCTTGCTGTCCTTGATCAGGCAGCCACCAAAAGCGATGTC<br>GGTGCCGTCGATCCCAACGGTGATATTGTCACTGGTGTGGCCGGGGCCG<br>GGGTAAAATACCTTGAGCGGGCCAAAGTTGGGCGCGGTTGCTGGTTCG<br>ACCCAGCCATTGGCGGCGAAAGTCAGGCTGTGTTGCGCCGCAACCATCC<br>CCTCTTGCGGGGCAAGCTGGTTCGACAACGCATTGGCATAAGTCGCAAT<br>CCCCGCCGCATGCAGCGCGTCCATACCGCCCATCTTGTCCTGATGCGCG<br>TGAGTCACCACCGCCAGCGCGACCGGCAGGTTGATCTCCTGCTTGATCC<br>AGTTGAGGATCTGGGCGGTCTGGTCATCGGTCCAGGCGGTATCGACCAC<br>CAGCACGCGGCCGCCATCCCTGACGATCAAACCGTTGGAAGCGACTGC<br>CCCGAAACCCGGCATGTCGAGATAGGAAGTGTGCTGCCAGACATTCGG<br>TGCGAGCTGGCGGAAAACCAGATCGCCAAACCGTTGGTCGCCAGTTTCC | SEQ ID NO 12 |

TABLE 1-continued

| Target Resistance Gene Sequences | | |
|---|---|---|
| | ATTTGCTGGCCAATCGTCGGGCGGATTTCACCGGGCATGCACCCGCTCA<br>GCATCAATGCAGCGGCTAATGCGGTGCTCAGCTTCGCGACCGGGTGCAT<br>AATATTGGGCAATTCCATCAAGTTTTCCTTTTATTCAGCATTAAAAACCC<br>CGCAAATGCGAGGCCTAGTAAATAGATGATCTTAATTTGGTTCACTGTA<br>GCAAAAATATGGGGCGAATTCAAACATGAGGTGCGACAGTTTCAA | |
| $bla_{SHV\text{-}18}$ | TTGTGAATCAGCAAAACGCCGGGTTATTCTTATTTGTCGCTTCTTTACTC<br>GCCTTTATCGGCCCTCACTCAAGGATGTATTGTGGTTATGCGTTATTTTC<br>GCCTGTGTATTATCTCCCTGTTAGCCACCCTGCCGCTGGCGGTACACGC<br>CAGCCCGCAGCCGCTTGAGCAAATTAAACTAAGCGAAAGCCAGCTGTC<br>GGGCAGCGTAGGCATGATAGAAATGGATCTGGCCAGCGGCCGCACGCT<br>GACCGCCTGGCGCGCCGATGAACGCTTTCCCATGATGAGCACCTTTAAA<br>GTAGTGCTCTGCGGCGCAGTGCTGGCGCGGGTGGATGCCGGTGACGAA<br>CAGCTGGAGCGAAAGATCCACTATCGCCAGCAGGATCTGGTGGACTAC<br>TCGCCGGTCAGCGAAAAACACCTTGCCGACGGCATGACGGTCGGCGAA<br>CTCTGTGCCGCCGCCATTACCATGAGCGATAACAGCGCCGCCAATCTGC<br>TGCTGGCCACCGTCGGCGGCCCCGCAGGATTGACTGCCTTTTTGCGCCA<br>GATCGGCGACAACGTCACCCGCCTTGACCGCTGGGAAACGGAACTGAA<br>TGAGGCGCTTCCCGGCGACGCCCGCGACACCACTACCCCGGCCAGCAT<br>GGCCGCGACCCTGCGCAAGCTGCTGACCAGCCAGCGTCTGAGCGCCCG<br>TTCGCAACGGCAGCTGCTGCAGTGGATGGTGGACGATCGGGTCGCCGG<br>ACCGTTGATCCGCTCCGTGCTGCCGGCGGGCTGGTTTATCGCCGATAAG<br>ACCGGAGCTGCCAAACGGGGTGCGCGCGGGATTGTCGCCCTGCTTGGC<br>CCGAATAACAAAGCAGAGCGGATTGTGGTGATTTATCTGCGGGATACG<br>CCGGCGAGCATGGCCGAGCGAAATCAGCAAATCGCCGGGATCGGCGCG<br>GCGCTGATCGAGCACTGGCAACGCTAACCCGGCGGTGGCCGCGCGCGT<br>TATCCGGCTCGTAG | SEQ ID<br>NO 13 |
| vanC-2 | GACTGAATGTAGTAAGAATCGAAAAGCGGAAGGAAGAAAAACATGAA<br>AAAAATCGCCATTATTTTTGGAGGCAATTCACCGGAATACACCGTTTCT<br>TTAGCTTCAGCAACTAGCGCAATCGAAGCACTCCAATCATCTCCCTATG<br>ACTACGACCTCTCTTTGATCGGGATCGCCCCAGATGCTATGGATTGGTA<br>CTTGTATACAGGAGAACTGGAAAACATCCGACAAGACACGTGGTTGTT<br>GGATACGAAACATAAACAGAAAATACAGCCGCTATTCGAAGGAAACGG<br>CTTTTGGCTAAGTGAAGAGCAGCAAACGTTGGTACCTGATGTTTTATTT<br>CCCATTATGCATGGCAAATACGGGGAAGATGGCAGTATCCAAGGATTG<br>TTTGAATTGATGAAGCTGCCTTATGTAGGCTGCGGGGTGGCAAGTTCTG<br>CCTTATGTATGAACAAATGGCTGCTGCATCAAGCTGCAGCAGCCATTGG<br>CGTACAAAGTGCTCCTACGATTCTCTTGACAAATCAAGCCAACCAGCAA<br>GAACAAATCGAAGCTTTTATCCAGACCCATGGCTTTCCAGTTTTCTTTAA<br>GCCTAATGAAGCGGGCTCCTCAAAAGGGATCACTAAAGTCACCTGCGTT<br>GAAGAAATCGCTTCTGCCTTAAAAGAAGCCTTTACTTATTGTTCCGCAG<br>TGCTCCTACAAAAAAATATTGTCGGTGTTGAGATCGGTTGCGGTATTTT<br>GGGCAACGACTCTTTGACTGTCGGTGCTTGTGACGCCATTTCATTAGAA<br>GACGGCTTTTTCGATTTTGAAGAAAAGTACCAGCTGATCAGCGCCAAAA<br>TCACCGTCCCTGCGCCATTGCCTGAAACGATTGAAACCAAGGTCAAAGA<br>ACAAGCTCAGCTGCTCTATCGTAGTCTTGGTCTTAAAGGTCTTGCTCGC<br>ATCGATTTTTTTGTCACGGATCAAGGAGAACTATACCTGAATGAAATCA<br>ATACTATGCCGGGCTTTACGAGTCACTCCCGCTATCCTGCCATGATGGC<br>AGCGGTCGGCTTATCCTATCAAGAACTACTACAAAAACTGCTTATCTTA<br>GCAAAGGAGGAAGTCAAATGAATCCCTATCTACAGTTAGTTAGCAAAA<br>AATTTCCGTTAGAAAAAAACCAAGAACCCCCTCATTTAGTCCTTGCTGC<br>CTTCAGCGAAGACGAGGTTTACTTGCAGC | SEQ ID<br>NO 14 |

REFERENCES

1. Wagner, E. G. H. and R. W. Simons, *Antisense RNA Control in Bacteria, Phages, and Plasmids*. Annual Review of Microbiology, 1994. 48(1): p. 713-742.
2. Nielsen, P. E., et al., *Peptide nucleic acids*. 1998, Google Patents.
3. Good, L. and P. E. Nielsen, *Progress in Developing PNA as a Gene-Targeted Drug. Antisense and Nucleic Acid Drug Development*, 1997. 7(4): p. 431-437.
4. Larsen, H. J., T. Bentin, and P. E. Nielsen, *Antisense properties of peptide nucleic acid*. Biochimica et Biophysica Acta (BBA)—Gene Structure and Expression, 1999. 1489(1): p. 159-166.
5. Nielsen, P., et al., *Sequence-selective recognition of DNA by strand displacement with a thymine-substituted polyamide*. Science, 1991.254(5037): p. 1497-1500.
6. Good, L. and P. E. Nielsen, *Antibiotic-free bacterial strain selection with antisense molecules*. 2002, Google Patents.
7. Mondhe, M., et al., *Species-Selective Killing of Bacteria by Antimicrobial Peptide-PNAs*. PLoS ONE, 2014. 9(2): p. e89082.
8. Garneau, J. E., et al., *The CRISPR/Cas bacterial immune system cleaves bacteriophage and plasmid DNA*. Nature, 2010. 468(7320): p. 67-71.
9. Rasmussen, C., H. Sperling-Petersen, and K. Mortensen, *Hitting bacteria at the heart of the central dogma: sequence-specific inhibition*. Microbial Cell Factories, 2007. 6(1): p. 1-26.
10. Citorik, R. J., M. Mimee, and T. K. Lu, *Sequence-specific antimicrobials using efficiently delivered RNA-guided nucleases*. Nat Biotech, 2014. 32(11): p. 1141-1145.
11. Eriksson, M., P. E. Nielsen, and L. Good, *Cell Permeabilization and Uptake of Antisense Peptide-Peptide Nucleic Acid (PNA) into Escherichia coli*. Journal of Biological Chemistry, 2002. 277(9): p. 7144-7147.

12. Institute, C. a. L. S., *Performance Standards for Antimicrobial Susceptibility Tests; Approved Standard-Eleventh Edition.* 2012: Wayne, Pa.
13. Institute, C. a. L. S., *Performance Standards for Antimicrobial Susceptibility Testing; Twenty Second Informational Supplement.* 2012: Wayne Pa.
14. Jinek, M., et al., *A Programmable Dual-RNA-Guided DNA Endonuclease in Adaptive Bacterial Immunity*. Science, 2012. 337(6096): p. 816-821.
15. Kawai, S., W. Hashimoto, and K. Murata, *Transformation of Saccharomyces cerevisiae and other fungi: Methods and possible underlying mechanism*. Bioengineered Bugs, 2010. 1(6): p. 395-403.
16. Yamakawa, M., F. Hishinuma, and N. Gunge, *Intact Cell Transformation of Saccharomyces cerevisiae by Polyethylene Glycol*. Agricultural and Biological Chemistry, 1985. 49(3): p. 869-871.
17. Leaw, S. N., et al., *Identification of Medically Important Yeast Species by Sequence Analysis of the Internal Transcribed Spacer Regions*. Journal of Clinical Microbiology, 2006. 44(3): p. 693-699.
18. Zhang, L., M. J. Leibowitz, and Y. Zhang, *Antisense oligonucleotides effectively inhibit the co-transcriptional splicing of a Candida group I intron in vitro and in vivo: Implications for antifungal therapeutics*. FEBS Letters, 2009. 583(4): p. 734-738.
19. Szittner, R., et al., *Bright stable luminescent yeast using bacterial luciferase as a sensor. Biochemical and Biophysical Research Communications,* 2003. 309(1): p. 66-70.

What is claimed:

1. A method for measuring a mechanism that imparts a non-susceptible phenotype, comprising:

providing a sample comprising an Enterobacteriaceae that is not susceptible to carbapenem;

contacting the sample with carbapenem;

contacting the Enterobacteriaceae with an oligonucleotide molecule that targets a gene associated with carbapenem resistance;

contacting the sample with a non-replicative transduction particle (NRTP) comprising a reporter nucleic acid molecule encoding a reporter molecule under conditions such that the NRTP inserts into the microorganism the reporter nucleic acid molecule and such that the reporter molecule provides a detectable indication of viability; wherein the NRTP is produced by a method comprising, (a) inducing a lytic phase of a bacterial cell packaging system, wherein said bacterial cell packaging system comprises: a host bacteria cell; a first nucleic acid construct inside the host bacteria cell, comprising of a bacteriophage genome having a non-functional packaging initiation site sequence, wherein the non-functional packaging initiation site sequence prevents packaging of the bacteriophage genome into the NRTP; and a second nucleic acid construct inside the host bacteria cell and separate from the first nucleic acid construct, comprising of a reporter nucleic acid molecule having a reporter gene and a bacteriophage gene that contains a functional packaging initiation site sequence for facilitating packaging of a replicon of the reporter nucleic add molecule into the NRTP, wherein the functional packaging initiation site sequence within the bacteriophage gene on the second nucleic acid construct complements the non-functional packaging initiation site sequence in the bacteriophage genome on the first nucleic acid construct; (b) allowing the replicon of the reporter nucleic acid molecule to be packaged to produce the NRTP; and (c) collecting a lysate comprising a plurality of NRTPs; and measuring the mechanism of carbapenem non-susceptibility for the Enterobacteriaceae based on the presence or absence of the detectable indication of viability of the Enterobacteriaceae when the Enterobacteriaceae is in contact with the carbapenem and the oligonucleotide molecule, wherein the presence of the detectable indication of viability indicates that the gene targeted by the oligonucleotide molecule is not the mechanism of carbapenem nonsusceptibility, and wherein the absence of the detectable indication of viability indicates that the gene targeted by the oligonucleotide molecule is the mechanism of carbapenem non-susceptibility.

2. The method of claim 1 wherein the reporter nucleic acid molecule is a gene encoding a light-emitting molecule and the detectable indication of viability is light emission.

3. The method of claim 1, wherein the oligonucleotide molecule is selected from the group consisting of a peptide nucleic acid (PNA), a peptide-PNA, a CRISPR RNA (crRNA), an antisense oligonucleotide, and a double-stranded RNA (dsRNA).

4. The method of claim 3 wherein the oligonucleotide molecule is selected from the group consisting of SEQ. ID NO 2, SEQ ID NO 3, a CRISPR/Cas9 System comprising SEQ ID NO 4, and, a CRISPR/Cas9 System comprising SEQ ID NO 5.

* * * * *